US012697359B2

(12) United States Patent
Bae et al.

(10) Patent No.: US 12,697,359 B2
(45) Date of Patent: Aug. 4, 2026

(54) COMPOSITION FOR PREVENTING HAIR LOSS AND PROMOTING HAIR GROWTH COMPRISING POSTBIOTIC COMPONENTS FROM HEAT-TREAT *LIMOSILACTOBACILLUS FERMENTUM* LM1020

(71) Applicant: LACTOMASON CO., LTD., Jinju-si (KR)

(72) Inventors: Won Young Bae, Seoul (KR); So Lim Shin, Anyang-si (KR); Woo Hyun Jung, Seoul (KR); Tae Rahk Kim, Suwon-si (KR)

(73) Assignee: LACTOMASON CO., LTD., Jinju-si (KR)

( * ) Notice: Subject to any disclaimer, the term of this patent is extended or adjusted under 35 U.S.C. 154(b) by 109 days.

(21) Appl. No.: 18/770,789

(22) Filed: Jul. 12, 2024

(65) Prior Publication Data

US 2024/0390437 A1        Nov. 28, 2024

Related U.S. Application Data

(63) Continuation       of       application       No. PCT/KR2023/016535, filed on Oct. 24, 2023.

(30) Foreign Application Priority Data

May 23, 2023     (KR) ........................ 10-2023-0066317

(51) Int. Cl.
| | |
|---|---|
| *A61K 35/747* | (2015.01) |
| *A61K 8/34* | (2006.01) |
| *A61K 8/365* | (2006.01) |
| *A61K 8/42* | (2006.01) |
| *A61K 8/99* | (2017.01) |
| *A61P 17/14* | (2006.01) |
| *A61Q 7/00* | (2006.01) |

(52) U.S. Cl.
CPC .............. *A61K 35/747* (2013.01); *A61K 8/34* (2013.01); *A61K 8/365* (2013.01); *A61K 8/42* (2013.01); *A61K 8/99* (2013.01); *A61P 17/14* (2018.01); *A61Q 7/00* (2013.01); *A61K 2800/782* (2013.01); *A61K 2800/85* (2013.01)

(58) Field of Classification Search
CPC ........ A61K 35/747; A61K 8/34; A61K 8/365; A61K 8/42; A61K 8/99; A61K 2800/782; A61K 2800/85; A61K 8/978; A61K 8/9789; A61P 17/14; A61Q 7/00
See application file for complete search history.

(56) References Cited

FOREIGN PATENT DOCUMENTS

| | | | |
|---|---|---|---|
| CN | 115624573 | A | 1/2023 |
| JP | 2018-035136 | A | 3/2018 |
| JP | 2018-529720 | A | 10/2018 |
| KR | 1020150072327 | A | 6/2015 |
| KR | 1020170038462 | A | 4/2017 |
| KR | 1020170100828 | A | 9/2017 |
| KR | 101790548 | B1 | 10/2017 |
| KR | 101791088 | B1 | 10/2017 |
| KR | 101840376 | B1 | 3/2018 |
| KR | 102004346 | B1 | 7/2019 |
| KR | 1020230062143 | A | 5/2023 |
| KR | 102578662 | B1 | 9/2023 |

OTHER PUBLICATIONS

Hosein Rastegar et al. Herbal Extracts Induce Dermal Papilla Cell Proliferation of Human Hair Follicles. Annals of Dermatology. Dec. 2015, vol. 27, No. 6, pp. 667-675.
Sole Cho et al. Antioxidative Activity and Protein Expression Effects of the Extracts from Cinnamomum camphora on the Hair growth Relevant Factors. Asian Journal of Beauty & Cosmetology. 2016, vol. 14, No. 1, pp. 18-29.
Zhang et al. Epidermal Growth Factor Promotes Proliferation and Migration of Follicular Outer Root Sheath Cells via Wnt/β Catenin Signaling. Cellular Physiology and Biochemistry. 2016, vol. 39, No. 1, pp. 306-370.
International Search Report of PCT/KR2023/016535 dated Feb. 20, 2024.

*Primary Examiner* — Kade Ariani
(74) *Attorney, Agent, or Firm* — NKL LAW; Jae Youn Kim

(57)        ABSTRACT

The present disclosure relates to heat-treated *Limosilactobacillus fermentum* LM1020 for preventing hair loss and promoting hair growth, and more particularly, to heat-treated *Limosilactobacillus fermentum* LM1020 for preventing hair loss and promoting hair growth by promoting the proliferation of dermal papilla cells and a composition containing the same. Heat-treated *Limosilactobacillus fermentum* LM1020 of the present disclosure and a composition containing the same promotes the proliferation of dermal papilla cells, has excellent 5α-reductase-1 inhibitory activity, and promotes the expression of FGF7, FGF10, and EGF, which are growth factors, and thus have the effect of effect of preventing hair loss and promoting hair growth. The subject cell line referred to as *Lactobacillus fermentum* LM1020 has the International Depositary Authority accession number KCCM12918P, having been deposited on Dec. 23, 2020.

17 Claims, 19 Drawing Sheets

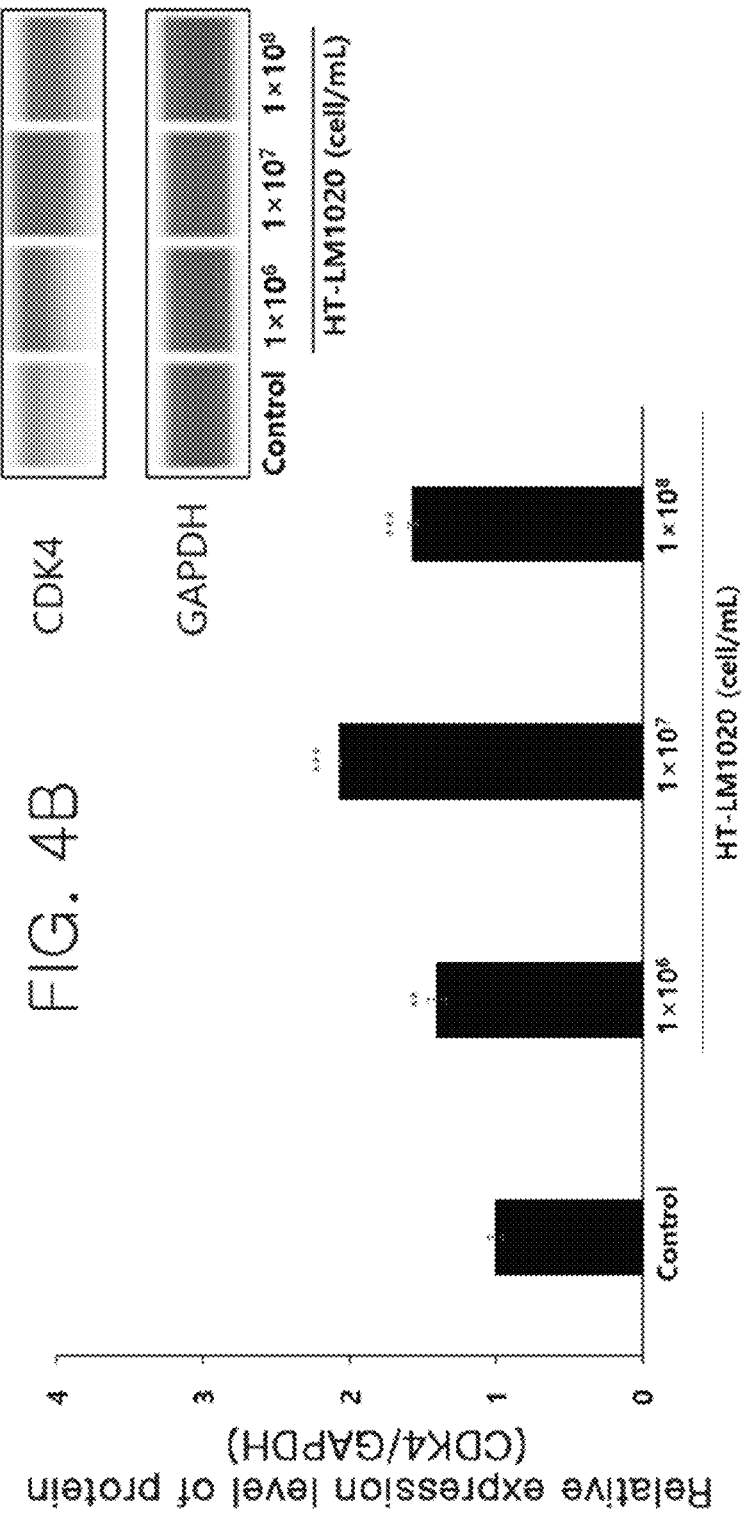

COMPOSITION FOR PREVENTING HAIR LOSS AND PROMOTING HAIR GROWTH COMPRISING POSTBIOTIC COMPONENTS FROM HEAT-TREAT *LIMOSILACTOBACILLUS FERMENTUM* LM1020

TECHNICAL FIELD

The present disclosure relates to heat-treated *Limosilactobacillus fermentum* LM1020 for preventing hair loss and promoting hair growth, and more particularly, to heat-treated *Limosilactobacillus fermentum* LM1020 for preventing hair loss and promoting hair growth by promoting the proliferation of dermal papilla cells and a composition containing the same.

BACKGROUND

Hair loss refers to a state in which hairs are not present in regions which should have hair. In general, hair loss refers to loss of terminal hairs from the scalp. In the past, hair loss was regarded as a men's issue. However, in the modern society, the number of women worrying about hair loss has been increasing and the age at which hair loss occurs has gradually been lowered. As the number of patients with hair loss has increased, studies on the causes of, countermeasures against and medicines for hair loss have attracted attention.

For example, Minoxidil and Propecia are currently the most effective medicines for preventing or treating hair loss. However, Minoxidil affects body hairs on the whole body and thus causes body hairs on the whole body as well as hair to grow darker and thicker. Also, Minoxidil lowers blood pressure, and, thus, those with low blood pressure should refrain from taking Minoxidil. Further, Minoxidil is metabolized in the liver, and, thus, those with liver disorders should also refrain from taking Minoxidil. Furthermore, Propecia is a male hormone, and, thus, women is prohibited from taking Propecia. Also, Propecia is known to have side effects, such as loss of libido or sexual dysfunction, and it was recently reported to cause depression and mood changes in patients given Propecia, which was added to precautions. In this regard, there is a demand for medicines for hair loss which exhibit better effects with fewer side effects than Minoxidil and Propecia.

Meanwhile, microbial resources are renewable unlike petroleum, water, etc. and thus classified as sustainable resources, and are highly applicable to researches and industries since the intrinsic characteristics of microorganisms that adapt to various environments are utilized. In particular, postbiotics refer to strain-derived components which are inactivated by heat treatment or the like, but can provide health benefits. Postbiotics have effects on immunoregulation, skin condition improvement, antioxidation, and inflammation control. Also, since postbiotics are inactivated, they are better than probiotics in terms of stability, safety, economic efficiency, storage efficiency, etc.

The skin surface and the openings of hair follicles are rich in microbial communities and recognized for strong immune activation. Also, there is a strong correlation between immune privileged sites essential for the hair cycle and microbial communities. Changes in the microbiome or absorption of microbial metabolites in the hair follicles are related to the inflammatory response of the hair follicles, such as regulation of skin immune response and homeostasis. When folliculitis is relieved, the possibility of hair regrowth increases. Therefore, management of the microbiome in the local scalp surface is very important for hair loss and hair growth.

In this regard, products are being developed using microorganisms for applications to hair loss patients rapidly increasing in recent years to prevent hair loss and promote hair growth. Korea Patent Laid-open Publication No. 10-2017-0038462 discloses one of the examples thereof. However, research on the exact mechanism of hair growth regulation by dermal papilla cells or new modulators is still insufficient.

Accordingly, the present inventors conducted research on a composition for preventing hair loss or promoting hair growth that can promote the proliferation of dermal papilla cells (HDPCs). As a result, the present inventors verified that heat-treated *Limosilactobacillus fermentum* LM1020 (KCCM12918P) promotes the proliferation of dermal papilla cells and thus completed the present disclosure. Under the provisions of the Budapest Treaty on the International Recognition of the Deposit of Microorganisms for the Purposes of Patent Procedure, the strains *Lactobacillus fermentum* LM1020 was deposited with the international depositary authority, the Korean Culture Center of Microorganisms, on Dec. 23, 2020, under the Accession Number KCCM12918P.

DISCLOSURE OF THE INVENTION

Problems to be Solved by the Invention

The present disclosure is conceived to provide a composition comprising heat-treated *Limosilactobacillus fermentum* LM1020 (KCCM12918P), which has the effect of preventing hair loss and promoting hair growth.

However, the problems to be solved by the present disclosure are not limited to the above-described problems. Although not described herein, other problems to be solved by the present disclosure can be clearly understood by a person with ordinary skill in the art from the following descriptions.

Means for Solving the Problems

A first aspect of the present disclosure provides a cosmetic composition for proliferating dermal papilla cells, comprising heat-treated *Limosilactobacillus fermentum* LM1020 (KCCM12918P) as an active ingredient.

A second aspect of the present disclosure provides a food composition for proliferating dermal papilla cells, comprising heat-treated *Limosilactobacillus fermentum* LM1020 (KCCM12918P) as an active ingredient.

A third aspect of the present disclosure provides a pharmaceutical composition for treating hair loss, comprising heat-treated *Limosilactobacillus fermentum* LM1020 (KCCM12918P) as an active ingredient.

Effects of the Invention

Heat-treated *Limosilactobacillus fermentum* LM1020 of the present disclosure and a composition containing the same promotes the proliferation of dermal papilla cells, has excellent 5α-reductase-1 inhibitory activity, and promotes the expression of FGF7, FGF10, and EGF, which are growth factors, and thus have the effect of effect of preventing hair loss and promoting hair growth.

3

BRIEF DESCRIPTION OF THE DRAWINGS

FIG. 4B shows the changes in expression level of CDK4 in dermal papilla cells after treatment with heat-treated *Limosilactobacillus fermentum* LM1020.

4

Figure 7A:
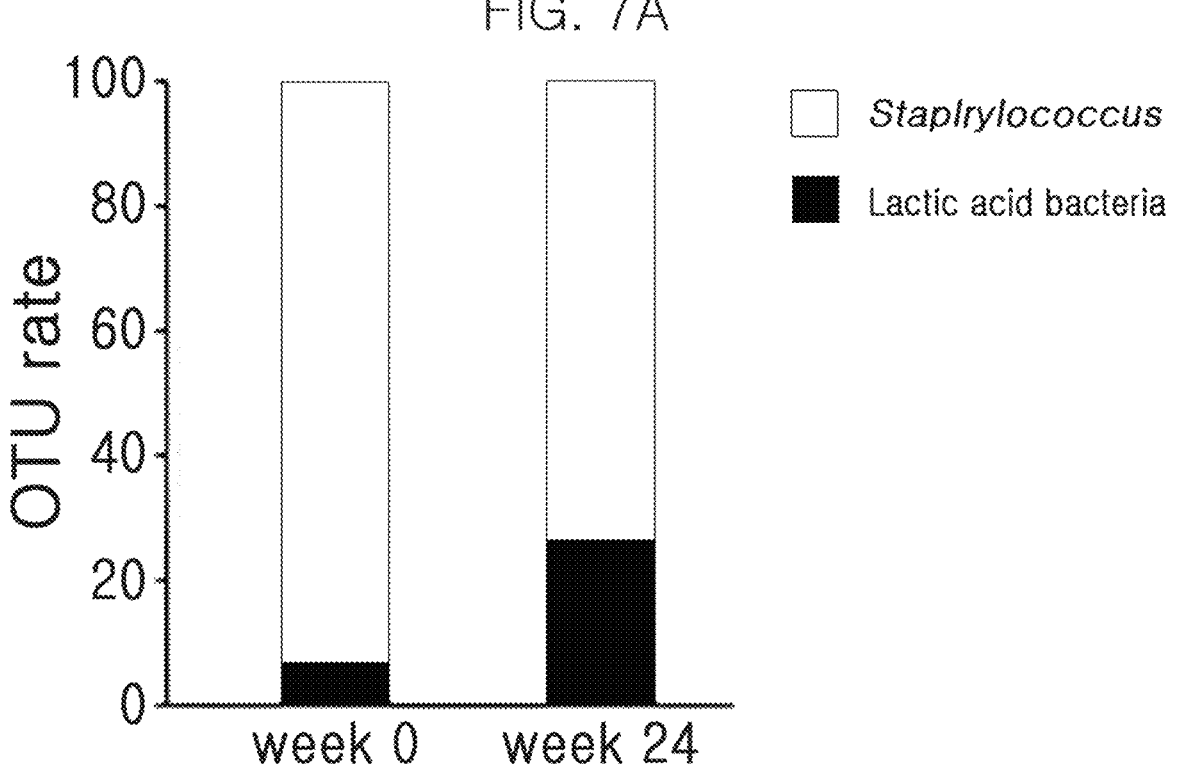
FIG. 7A shows the changes in ratio (operational taxonomy unit) between *Staphylococcus* and lactic acid bacteria in the scalp of participants before and after the use of a product containing heat-treated *Limosilactobacillus fermentum* LM1020.
Figure 7B:
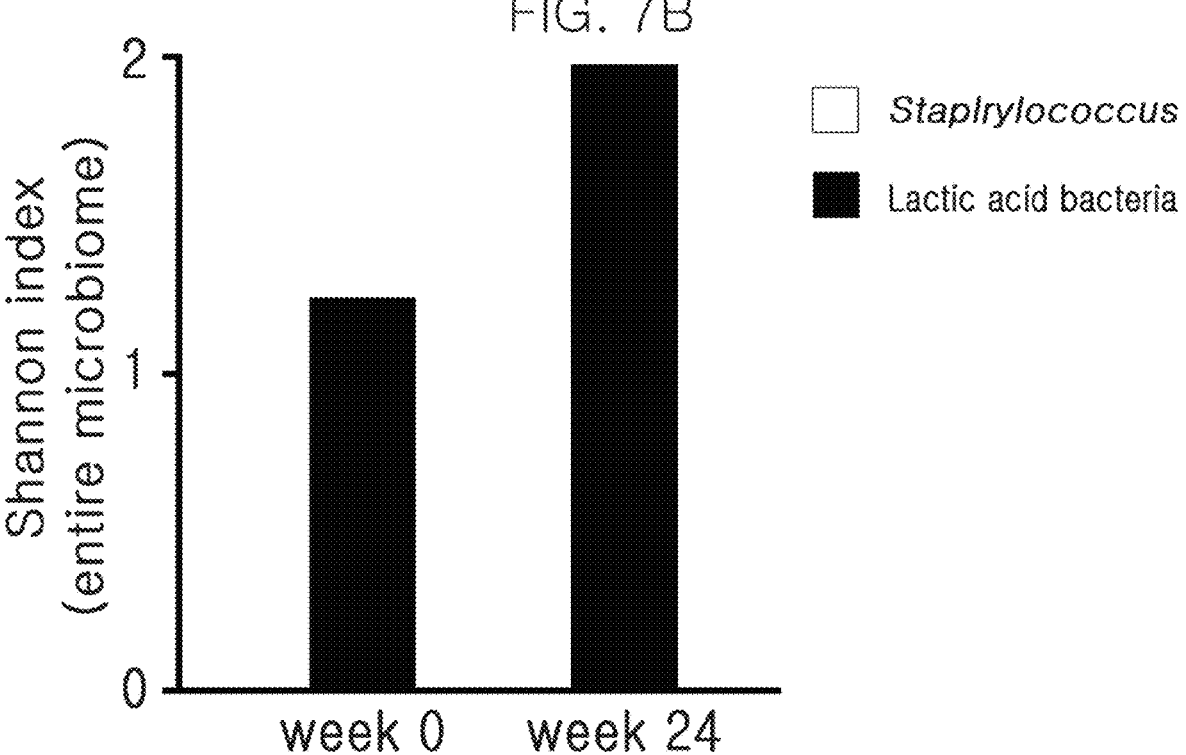
FIG. 7B shows the changes in Shannon index of *Staphylococcus* and lactic acid bacteria with respect to the entire microbiome in the scalp of participants before and after the use of a product containing heat-treated *Limosilactobacillus fermentum* LM1020.
Figure 7C:
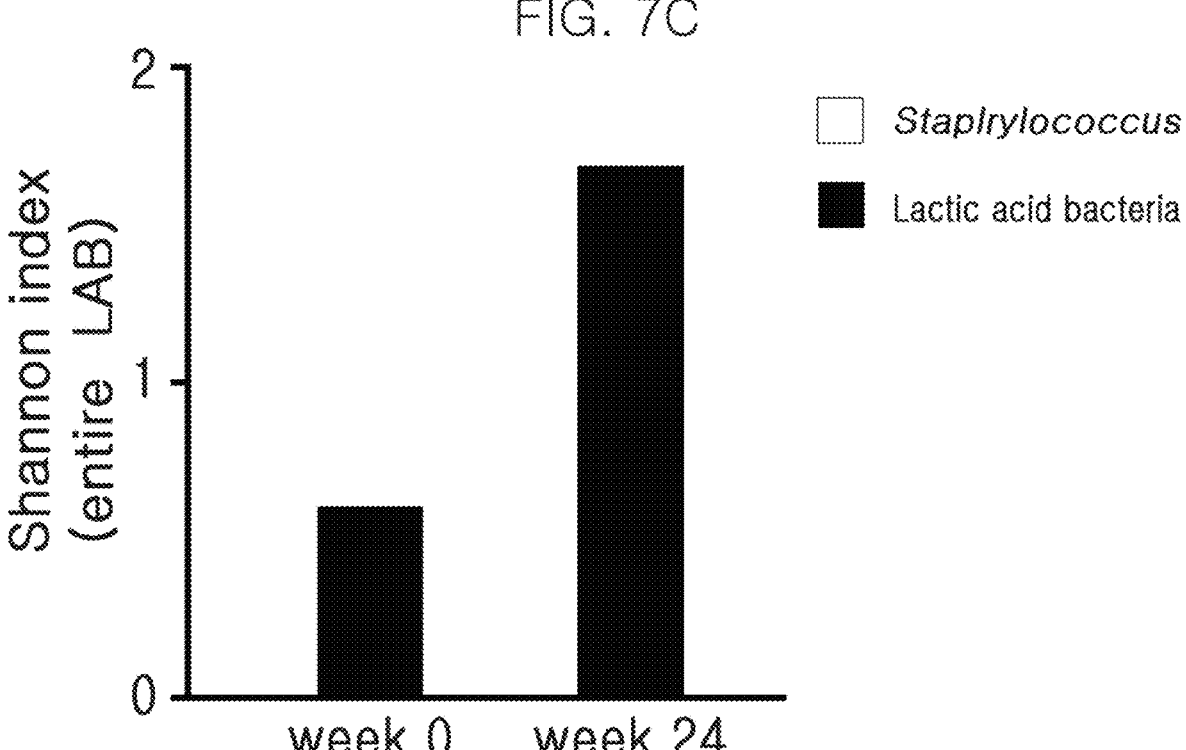
FIG. 7C shows the changes in Shannon index of *Staphylococcus* and lactic acid bacteria with respect to all lactic acid bacteria (LAB) in the scalp of participants before and after the use of a product containing heat-treated *Limosilactobacillus fermentum* LM1020.
Figure 7D:
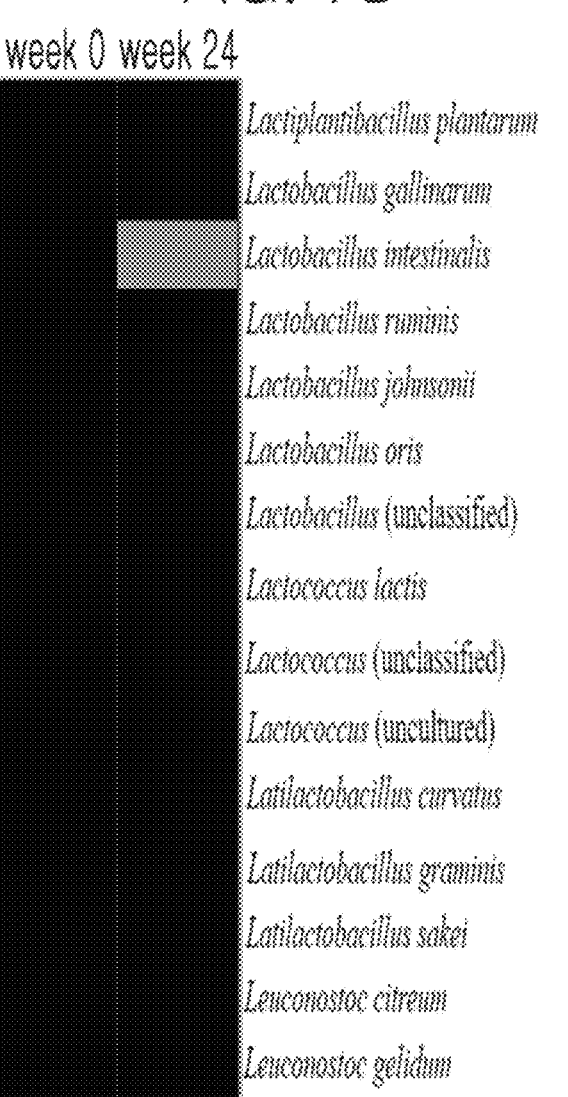

FIG. 7D shows the changes in major microorganisms in the scalp of participants before and after the use of a product containing heat-treated *Limosilactobacillus fermentum* LM1020.

Figure 7E:
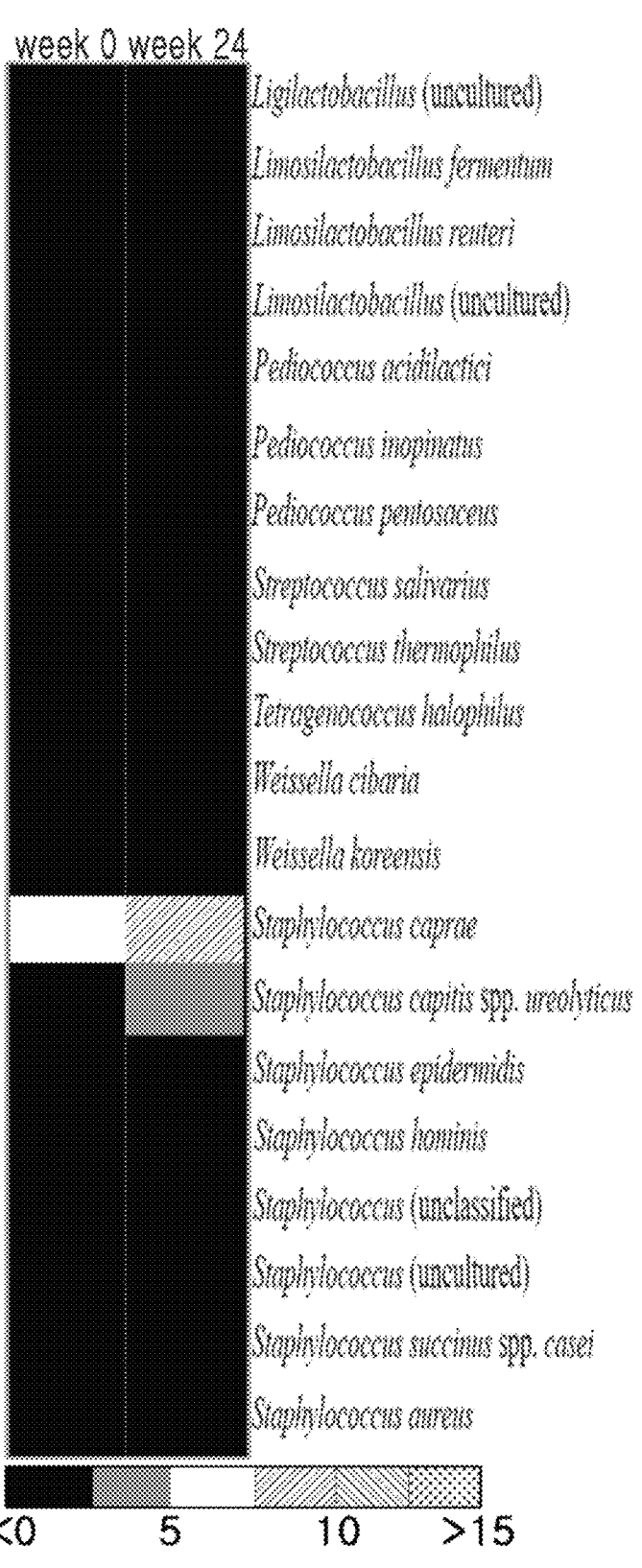

FIG. 7E shows the changes in major microorganisms in the scalp of participants before and after the use of a product containing heat-treated *Limosilactobacillus fermentum* LM1020.

BEST MODE FOR CARRYING OUT THE INVENTION

Hereafter, examples of the present disclosure will be described in detail with reference to the accompanying drawings so that the present disclosure may be readily implemented by a person with ordinary skill in the art. However, it is to be noted that the present disclosure is not limited to the examples but can be embodied in various other ways. In the drawings, parts irrelevant to the description are omitted for the simplicity of explanation, and like reference numerals denote like parts through the whole document.

Through the whole document, the term 'comprises or includes' and/or 'comprising or including' used in the document means that one or more other components, steps, operation and/or existence or addition of elements are not excluded in addition to the described components, steps, operation and/or elements unless context dictates otherwise.

Through the whole document, the term 'about or approximately' or 'substantially' is intended to have meanings close to numerical values or ranges specified with an allowable error and intended to prevent accurate or absolute numerical values disclosed for understanding of the present disclosure from being illegally or unfairly used by any unconscionable third party.

Through the whole document, the term 'step of' does not mean 'step for'.

Through the whole document, the term 'combination(s) of' included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Hereinafter, embodiments and examples of the present disclosure will be described in detail with reference to the accompanying drawings. However, the present disclosure may not be limited to the following embodiments, examples, and drawings.

A first aspect of the present disclosure provides a cosmetic composition for proliferating dermal papilla cells, comprising heat-treated *Limosilactobacillus fermentum* LM1020 (KCCM12918P) as an active ingredient.

Through the whole document, the term "heat-treated lactic acid bacteria" refer to heat-killed bacteria which are inactivated by heat treatment of *Limosilactobacillus fermentum* LM1020.

Through the whole document, the term "heat-killed bacteria" is opposite to the term "live bacteria" and refers to bodies obtained by suppressing the growth of bacteria such as heat-treating live bacteria obtained by fermentation and metabolites thereof. The heat-killed bacteria may contain cytoplasm, cell wall, antibacterial substances such as bacteriocin, polysaccharides, organic acid, and the like. Products using the heat-killed bacteria have higher stability than live bacteria products and are particularly excellent in heat resistance and have high stability to the external environment. Therefore, the products using the heat-killed bacteria are easier to store and have longer shelf life than the existing live bacteria products. Further, since the regulations on the use of antibiotics become stricter, there are a handful of companies that have produced heat-killed bacteria products. Therefore, considering the application as substitutes and the number of the producing companies, the marketability and growth potential is very high.

In an embodiment of the present disclosure, a component derived from the strain *Limosilactobacillus fermentum* LM1020 may be derived from fermented dough but may not be limited thereto.

In an embodiment of the present disclosure, the heat-treated *Limosilactobacillus fermentum* LM1020 may have a ratio of saturated fatty acids:unsaturated fatty acids:cyclic fatty acids of 0.1 to 2:0.25 to 5:0.03 to 0.6, and preferably 1:2.5:0.3, but may not be limited thereto.

In an embodiment of the present disclosure, the heat-treated *Limosilactobacillus fermentum* LM1020 may increase the expression of CDK2, CDK4, cyclin B1, and cyclin D1.

In an embodiment of the present disclosure, the heat-treated *Limosilactobacillus fermentum* LM1020 may reduce a gene expression level of 5α-reductase-1 and increase gene expression levels of FGF7, FGF10, and EGF.

In an embodiment of the present disclosure, the cosmetic composition for proliferating dermal papilla cells may further contains L-menthol, salicylic acid, and dexpanthenol.

In an embodiment of the present disclosure, when the heat-treated *Limosilactobacillus fermentum* LM1020 is used for treatment together with compounds of L-menthol, salicylic acid, and dexpanthenol, the effect of promoting the growth of dermal papilla cells is improved as compared to when the heat-treated *Limosilactobacillus fermentum* LM1020 is used alone.

In an embodiment of the present disclosure, the heat-treated *Limosilactobacillus fermentum* LM1020 may have a concentration of $1\times10^4$ cells/mL to $1\times10^8$ cells/mL, preferably $1\times10^6$ cells/mL to $1\times10^7$ cells/mL, and more preferably $1\times10^6$ cells/mL or $1\times10^7$ cells/mL but may not be limited thereto.

In an embodiment of the present disclosure, the cosmetic composition for proliferating dermal papilla cells may further contain purified water, ethanol, alanine/histidine/lysine polypeptide copper (HCl), polyacrylate crosspolymer-6, coconut acid, proline, tea tree oil, glycerin, peptide, butylene glycol, 1,2-hexanediol, green tea extracts, lavender flower extracts, quince extracts, and ethyl hexanediol. The cosmetic composition for proliferating dermal papilla cells may increase microbial diversity and lactic acid bacteria diversity of the scalp.

A second aspect of the present disclosure provides a food composition for proliferating dermal papilla cells, comprising heat-treated *Limosilactobacillus fermentum* LM1020 (KCCM12918P) as an active ingredient. The features described above in respect of the first aspect of the present disclosure may equally apply to the food composition according to the second aspect of the present disclosure.

Through the whole document, the term 'food' may include meats, sausages, breads, chocolates, candies, snacks, cookies, pizza, ramens, other noodles, gums, dairy products including ice cream, soups, beverages, teas, drinks, alcohol drinks, vitamin complexes, health functional foods and health foods, and may include all foods in the accepted meaning.

Through the whole document, the term 'health functional food' refers to foods prepared and processed using raw materials or ingredients having useful functions to the human body in accordance with the Health Functional Food Act, No. 6727, and the 'functionality' refers to adjusting nutrients on a structure and a function of the human body or obtaining a useful effect for health such as a physiological action.

The food of the present disclosure can be manufactured by conventional methods used in the art, and can be manufactured by adding conventional raw materials and ingredients used in the art. Further, a formulation of the food is not limited as long as the formulation is accepted as a food. The food composition of the present disclosure may be prepared in a variety of formulations. Since the food is used as raw materials, unlike general drugs, the food composition is free from side effects which may occur when a drug is taken for a long time and may have excellent portability.

The health functional food refers to a food having effects of actively maintaining or promoting health conditions, as compared with general foods, and a health supplement food refers to a food for supplementing health. If necessary, the health functional food, health food and health supplement food may be interchangeably used with each other. Specifically, the health functional food is a food prepared by adding the *Limosilactobacillus fermentum* LM1020 strain(s) of the present disclosure such as beverages, teas, spices, gums, confectionery, etc., or prepared in a capsule, a powder, or a suspension form. The health functional food means that it has a specific effect on health when consumed, but unlike general drugs, the health functional food is free from side effects that may occur when a drug is taken for a long time since the food is used as raw materials.

Since the food of the present disclosure could be consumed on a daily basis, a high effect can be expected to improve depression, so it can be very useful.

The food composition may further contain a physiologically acceptable carrier. The kind of the carrier is not particularly limited. Any carrier may be used as long as it is commonly used in the art.

Further, the food composition may further contain additional ingredients that are commonly used in food compositions so as to improve smell, taste, visuality, etc. For example, the food composition may contain vitamins A, C, D, E, B1, B2, B6, B12, niacin, biotin, folate, pantothenic acid, etc. Furthermore, the food composition may also contain minerals such as zinc (Zn), iron (Fc), calcium (Ca), chromium (Cr), magnesium (Mg), manganese (Mn), copper (Cu), chromium (Cr), etc. In addition, the cfood composition may contain amino acid such as lycin, tryptophan, cysteine, valine, etc.

Further, the food composition may also contain food additives, such as preservatives (potassium sorbate, sodium benzoate, salicylic acid, sodium dehydroacetate, etc.), disinfectants (bleaching powder, higher bleaching powder, sodium hypochlorite, etc.), antioxidants (butylhydroxyanisole (BHA), butylhydroxytoluene (BHT), etc.), colorants (tar color, etc.), color-developing agents (sodium nitrite, etc.), bleaching agents (sodium sulfite), seasonings (monosodium glutamate (MSG), etc.), sweeteners (dulcin, cyclemate, saccharin, sodium, etc.), flavors (vanillin, lactones, etc.), swelling agents (alum, potassium D-bitartrate, etc.), fortifiers, emulsifiers, thickeners (adhesive pastes), film-forming agents, gum base agents, antifoaming agents, solvents, improvers, etc. The additives may be selected and used in an appropriate amount depending on the type of food.

The heat-treated *Limosilactobacillus fermentum* LM1020 of the present disclosure may be added as it is, or may be used in conjunction with other foods or food ingredients, and may be appropriately used according to a conventional method. The mixing amount of active ingredients may be appropriately determined depending on the purpose of use (prophylactic, health or therapeutic treatment). In general, when a food or a beverage is manufactured, the food composition of the present disclosure may be added in an amount of 50 parts by weight or less, specifically 20 parts by weight or less based on the total weight of the food or the beverage. However, when taken for the purpose of health and hygiene, the food composition may be contained in an amount below the range. In addition, since there is no safety problem, the active ingredients may be used in an amount above the range.

The food composition of the present disclosure may be used as, for example, a health beverage composition, and in this case, the health beverage composition may further contain various flavors or natural carbohydrates, as in common beverages. The natural carbohydrates may include monosaccharides such as glucose and fructose; disaccharides such as maltose and sucrose; polysaccharides such as dextrin and cyclodextrin; and sugar alcohols such as xylitol, sorbitol and erythritol. The sweeteners may be natural sweeteners such as thaumatin or a *stevia* extract; or synthetic sweeteners such as saccharin or aspartame. The natural carbohydrate may be generally used in an amount of from about 0.01 g to about 0.04 g, and specifically, from about 0.02 g to about 0.03 g based on 100 mL of the health beverage composition of the present disclosure.

In addition, the health beverage composition may contain various nutrients, vitamins, minerals, flavors, colorants, pectic acid and salts thereof, alginic acid and salts thereof, organic acid, protective colloidal thickeners, pH regulators, stabilizers, antiseptics, glycerin, alcohols or carbonating agents. Moreover, the health beverage composition may contain fruit flesh used to prepare natural fruit juices, fruit juice beverages or vegetable beverages. These ingredients may be used individually or in combination. A proportion of the additives is not critical but is generally selected from 0.01 part by weight to 0.1 part by weight per 100 parts by weight of the health beverage composition of the present disclosure.

The food composition of the present disclosure may contain the heat-treated *Limosilactobacillus fermentum* LM1020 of the present disclosure in a variety of % by weight as long as it can exhibit the effect of preventing hair loss and promoting hair growth. Specifically, the heat-treated *Limosilactobacillus fermentum* LM1020 of the present disclosure may be contained in an amount of 0.00001% by weight to 100% by weight or 0.01% by weight to 80% by weight based on the total weight of the food composition but may not be limited thereto.

In an embodiment of the present disclosure, the food composition may be a health functional food composition.

A third aspect of the present disclosure provides a pharmaceutical composition for treating hair loss, comprising heat-treated *Limosilactobacillus fermentum* LM1020 (KCCM12918P) as an active ingredient. The features described above in respect of the first and second aspects of the present disclosure may equally apply to the pharmaceutical composition according to the third aspect of the present disclosure.

In an embodiment of the present disclosure, the pharmaceutical composition may be formulated and used as formulations for oral administration such as powders, granules, tablets, capsules, suspensions, emulsions, syrups or aerosol, ointment, suppositories, or sterile injection solutions by conventional methods, respectively, but is not limited thereto.

In an embodiment of the present disclosure, the pharmaceutical composition may be formulated with generally used diluents or excipients such as fillers, bulking agents, binders, wetting agents, disintegrating agents, or surfactants, but may not be limited thereto.

In an embodiment of the present disclosure, solid formulations for oral administration may include tablets, pills, powders, granules or capsules, and these solid formulations may be prepared by mixing a component derived from the strain with at least one of excipients such as starch, calcium carbonate, sucrose, lactose, or gelatin. Except for the simple excipients, lubricants such as magnesium stearate or talc may be used, but the present disclosure may not be limited thereto.

In an embodiment of the present disclosure, liquid formulations for oral administration may include suspensions, solutions for internal use, emulsions and syrups, and may contain various excipients such as wetting agents, sweeteners, aromatics and preservatives in addition to generally used simple diluents such as water and liquid paraffin but may not be limited thereto.

In an embodiment of the present disclosure, formulations for parenteral administration may include sterilized aqueous solutions, water-insoluble excipients, suspensions, emulsions, lyophilized preparations, and suppositories, but may not be limited thereto. For example, the water insoluble excipients or suspensions may contain propylene glycol, polyethylene glycol, vegetable oil such as olive oil, injectable ester such as ethylolate, and the like, but may not be limited thereto. For example, the suppositories may contain witepsol, macrogol, tween 61, cacao butter, laurin butter, glycerol, gelatin, and the like, but may not be limited thereto.

The pharmaceutical composition according to an embodiment of the present disclosure may be a drug composition or a quasi-drug composition.

Through the whole document, the term "quasi-drug" refers to an article having a milder action than drugs, among articles being used for the purpose of diagnosis, treatment, improvement, alleviation, handling or prevention of human or animal diseases. For example, according to the Pharmaceutical Affairs Law, the quasi-drugs are those, excluding articles used as drugs, including articles used for the purpose of treating or preventing human or animal diseases and articles which have a mild action on or have no direct influence on the human body.

The quasi-drug composition of the present disclosure may be manufactured in a formulation selected from the group consisting of body cleanser, sanitizer, detergent, kitchen cleanser, detergent for cleaning, toothpaste, mouthwash, wet wipe, cleanser, soap, hand soap, hair cleanser, hair softener, humidifying filler, mask, ointment, or filter filler, but may not be limited thereto.

In an embodiment of the present disclosure, the pharmaceutical composition may be administered in a pharmaceutically effective amount. Through the whole document, the term "pharmaceutically effective amount" refers to an amount sufficient to treat or prevent diseases at a reasonable benefit/risk ratio applicable to any medical treatment or prevention. An effective dosage level may be determined depending on factors including severity of the disease, drug activity, a patient's age, body weight, health conditions, gender, sensitivity to the drug, administration time, administration route, and excretion rate of the composition of the present disclosure, duration of treatment, drugs blended with or co-administered with the composition of the present disclosure, and other factors known in the medical field. The pharmaceutical composition of the present disclosure may be administered individually or in combination with an ingredient known for treating intestinal diseases. It is important to administer an amount to obtain a maximum effect in a minimum amount without side effects by considering all the above-described factors.

In an embodiment of the present disclosure, an administration dose of the pharmaceutical composition may be determined by a person with ordinary skill in the art in view of purpose of use, severity of the disease, a patient's age, body weight, gender, medical history or the kind of a material used as an active ingredient. For example, the pharmaceutical composition of the present disclosure may be administered at a dose of from about 0.1 ng/kg to about 1,000 mg/kg, and preferably, from about 1 ng/kg to about 100 mg/kg per adult, and the administration frequency of the composition of the present disclosure is not particularly limited, but the composition may be administered once a day or several times a day in divided doses. The administration dose or the administration frequency does not limit the scope of the present disclosure in any aspect.

The pharmaceutical composition of the present application may be administered via, but not particularly limited to, intraperitoneal administration, intravenous administration, intramuscular administration, subcutaneous administration, intradermal administration, transdermal patch administration, oral administration, intranasal administration, intrapulmonary administration, rectal administration, etc. depending on the purpose. However, when the pharmaceutical composition is administered via oral administration, it can be administered in an unformulated form, and since the strain(s) of the present disclosure can be denatured or degraded by gastric acid, the composition for oral administration may be coated with an active drug, formulated to be protected from degradation in the stomach, or formulated in the form or an oral patch. Also, the composition may be administered by any device capable of delivering an active ingredient to a target cell.

MODE FOR CARRYING OUT THE INVENTION

Hereinafter, the present disclosure will be explained in more detail with reference to Examples. However, the following Examples are illustrative only for better understanding of the present disclosure, but do not limit the present disclosure.

EXAMPLES

Example 1. Comparison of Effect of Heat-Treated Lactic Acid Bacteria on Proliferation of Dermal Papilla Cells Dermal papilla cells were purchased from PromoCell GmbH, seeded in flasks at a concentration of 5,000 to 10,000 cells/cm$^2$ and cultured. The dermal papilla cells were cultured in dermal papilla cell culture media prepared by adding growth factors (40 L/mL of fetal calf serum, 4 μL/mL of bovine pituitary extract, 1 ng/ml of fibroblast growth factor, 5 μg/mL of insulin) to commercial basal media at 37° C. with a CO$_2$ concentration maintained at 5%. When the dermal papilla cells reached a confluency of 80 to 90%, they were subcultured and used for test. The dermal papilla cells used in research were stored in liquid nitrogen for 2 to 5 generations and were used in the test for up to 10 generations.

The effect of heat-treated lactic acid bacteria on the promotion of proliferation of dermal papilla cells was verified by observing viable cells under a microscope through Trypan Blue staining. The dermal papilla cells that reached a confluency of 80 to 90% were seeded in a 24-well plate at a concentration of 100,000 cells/well and cultured for 24 hours. Then, the dermal papilla cells were treated with 1×10$^7$ cells/mL of heat-treated lactic acid bacteria to increase the number of cells compared to the control group. The number of cells was confirmed by directly counting under a microscope. The heat-treated lactic acid bacteria used to compare the effect of promoting the proliferation of dermal papilla cells included *Lactiplantibacillus plantarum* LP1001, *Lactococcus lactis* LP1009, *Lacticaseibacillus rhamnosus* LP1011, *Lacticaseibacillus paracasei* LP1014, and *Bifidobacterium animalis lactis* LP1017, *Limosilactobacillus fermentum* LP1016, *Limosilactobacillus fermentum* LM1020, *Lactobacillus acidophilus* LP1060, and *Lactobacillus gasseri* LP1065.

Figure 1:
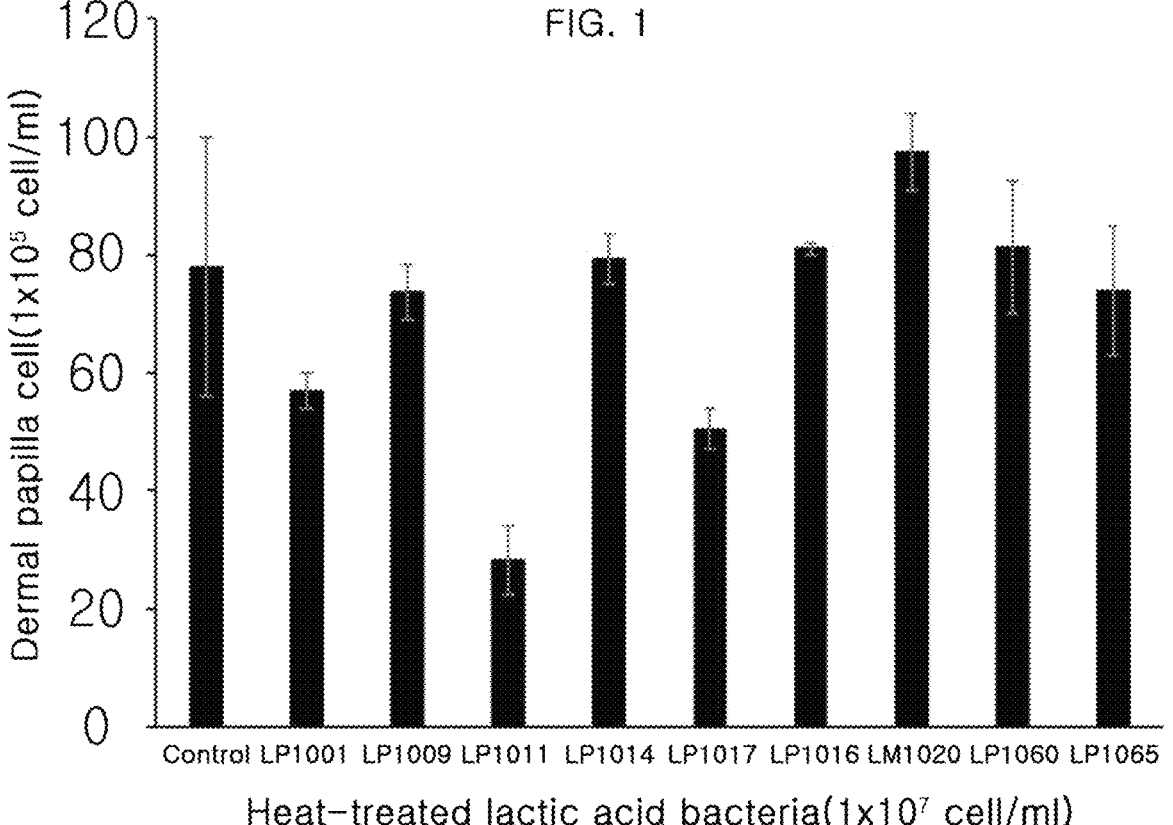
FIG. 1 shows the result of comparing the effect of heat-treated lactic acid bacteria on the promotion of proliferation of dermal papilla cells.

As a result of comparison, not all heat-treated lactic acid bacteria promoted the proliferation of dermal papilla cells. It was confirmed that among the 9 types of heat-treated lactic acid bacteria, only *Lacticaseibacillus paracasei* LP1014, *Lactobacillus acidophilus* LP1060, *Limosilactobacillus fermentum* LP1016, and *Limosilactobacillus fermentum* LM1020 were able to promote the growth of dermal papilla cells, while the other heat-treated lactic acid bacteria inhibited the growth of dermal papilla cells (FIG. 1).

*Limosilactobacillus fermentum* LP1016 and *Limosilactobacillus fermentum* LM1020 are conspecifics, but LP1016 is derived from kimchi and LM1020 is derived from fermented dough and thus have different origins from each other. As a result of research, even when heat-treated in the same manner, the heat-treated *Limosilactobacillus fermentum* LP1016 derived from kimchi improved the proliferation of dermal papilla cells by 3.7%, whereas the heat-treated *Limosilactobacillus fermentum* LM1020 derived from fermented dough improved the proliferation of dermal papilla cells by 24.9%.

Example 2. Bacterial Fatty Acid Composition of Heat-Treated Lactic Acid Bacteria Bacterial fatty acids are known to perform various functions in microorganism cells as precursors of intracellular membranous organelles including cell membranes. Methyl undecanoate, which does not exist in nature, was selected as internal standard (ISTD). It was prepared at a concentration of 10,000 μg/mL using HPLC grade n-hexane as a solvent, and then stored at −20° C. and diluted, as necessary, for use in research. To extract fatty acids from heat-treated lactic acid bacteria, 25 μℓ of the internal standard was added and 200 μℓ of a chloroform/methanol (2:1 (v/v)) mixed solution was added. Thereafter, for derivatization of fatty acids, 300 μℓ of a 0.6 M hydrochloric acid methanol solution was added, homogenized for 120 seconds, heated at 85° C. for 60 minutes, and allowed to cool at room temperature. After 1 mL of n-hexane was added again, it was homogenized for 120 seconds and left at room temperature for 60 to 120 minutes, and the supernatant was used for analysis. The fatty acids were analyzed by gas chromatography/mass spectrometer electron ionization method. Helium was used as the mobile phase, and a DB-FastFAME column was used as the column.

As a result, it was confirmed that the heat-treated *Limosilactobacillus fermentum* LP1016 and the heat-treated *Limosilactobacillus fermentum* LM1020, which are conspecifics but have different origins from each other, were different in bacterial fatty acid composition (Table 1). In particular, linoleate was present only in the heat-treated *Limosilactobacillus fermentum* LM1020, and behenic acid was present only in the heat-treated *Limosilactobacillus fermentum* LP1016. Among the fatty acids, oleate was about 2.4 times more abundant in the heat-treated *Limosilactobacillus fermentum* LM1020, and lactobacillic acid was about 2.1 times more abundant in the heat-treated *Limosilactobacillus fermentum* LP1016.

The two strains also differed greatly in the ratio of saturated and unsaturated fatty acids in the microorganism cells. *Limosilactobacillus fermentum* LP1016 derived from kimchi had a ratio of saturated fatty acids:unsaturated fatty acids:cyclic fatty acids of 1:1:0.6, whereas *Limosilactobacillus fermentum* LM1020 derived from fermented dough had a ratio of 1:2.5:0.3. Therefore, it was confirmed that the two strains had different fatty acid compositions and differed significantly in overall characteristics of the fatty acids.

TABLE 1

| Fatty acids | Contents (%) | |
| --- | --- | --- |
| | LM1016 | LM1020 |
| Laurate | 0.71 | 0.49 |
| Myristate | 1.15 | 1.21 |
| Pentadecanoate | 0.42 | 0.46 |
| Palmitate | 32.44 | 21.79 |
| Palmitoleate | 1.28 | 1.26 |
| Palmitelaidate | 1.34 | 1.37 |
| Margarate | 0.00 | 0.00 |
| Stearate | 3.37 | 2.08 |
| Oleate | 8.73 | 20.62 |
| cis-11-Vaccenate | 21.2 | 33.34 |
| Linoleate | 0.00 | 1.07 |
| cis-10-nonadecenoate | 9.08 | 8.54 |
| Lactobacillic acid | 16.54 | 7.77 |
| Arachidate | 0.00 | 0.00 |
| cis-11,14-Eicosadienoate | 0.00 | 0.00 |
| Behenic acid | 1.20 | 0.00 |
| Saturated fatty acid | 40.31 | 26.03 |
| Unsaturated fatty acid | 43.14 | 66.20 |
| Cyclic fatty acid | 25.69 | 7.77 |
| Unsaturated fatty acid/Saturated fatty acid | 1.07 | 2.54 |
| Unsaturated fatty acid + Cyclic fatty acid/ Saturated fatty acid | 1.48 | 2.84 |

Figure 2:
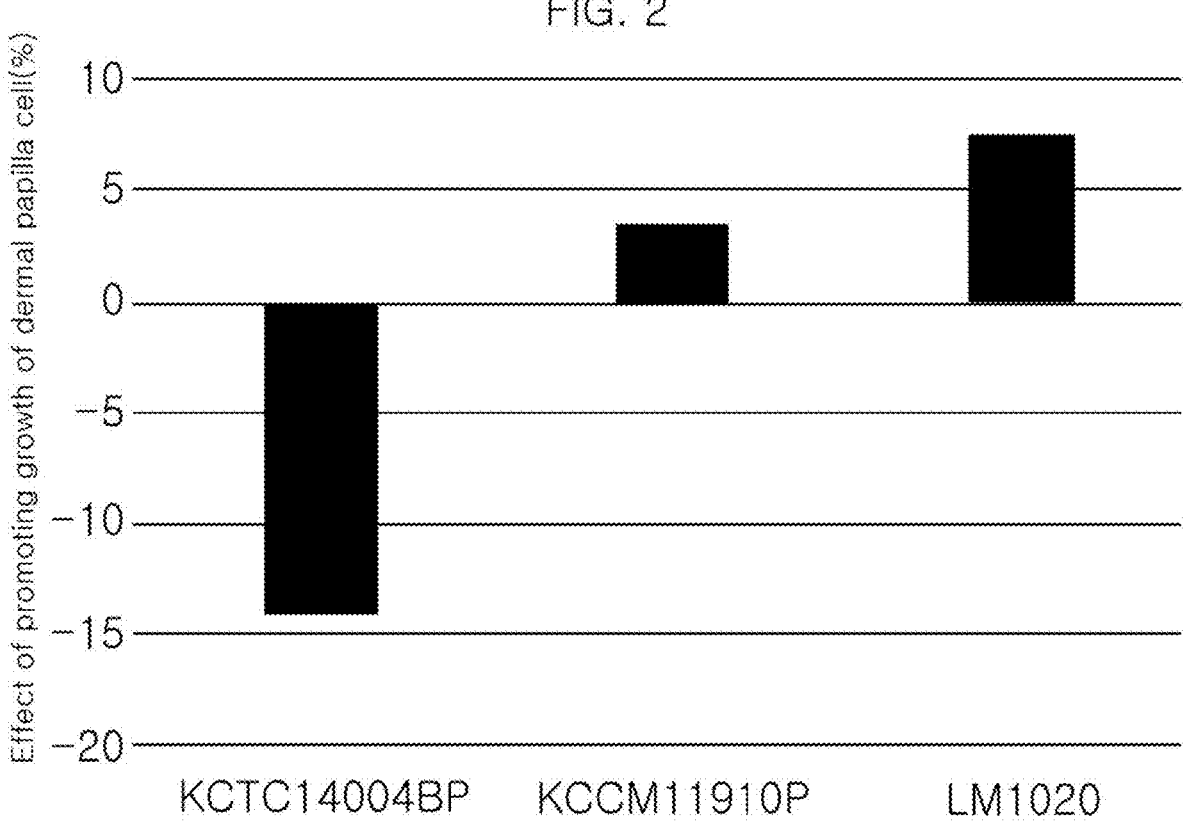
FIG. 2 shows the result of comparing the effect of heat-treated lactic acid bacteria on the promotion of growth of dermal papilla cells.

Example 3. Comparison of Effect of Heat-Treated Lactic Acid Bacteria on Promotion of Growth of Dermal Papilla Cells Through comparison with strains known to be effective in preventing hair loss or promoting hair growth (*Lacticaseibacillus paracasei* KCTC 14004BP and *Limosilactobacillus fermentum* KCCM 11910P), the effect of the heat-treated *Limosilactobacillus fermentum* LM1020 on the proliferation of dermal papilla cells was verified (FIG. 2).

All the strains used for comparison were inactivated by heat treatment at a high temperature of 121° C. for 15 minutes.

Dermal papilla cells (10,000 cells/well) were treated with heat-treated lactic acid bacteria at a concentration of $2.5 \times 10^7$ cells/mL and then cultured as in Example 1. The dermal papilla cell growth promotion effect was calculated using the formula below.

Through comparison between a growth rate when only dermal papilla cells were cultured and a growth rate when heat-treated lactic acid bacteria were added, the effect of heat-treated lactic acid bacteria on the promotion of growth of dermal papilla cells was confirmed. A growth rate when dermal papilla cells were cultured by the above-described method without any addition, and growth rates of dermal papilla cells when heat-treated *Lacticaseibacillus paracasei* KCTC 14004BP, heat-treated *Limosilactobacillus fermentum* KCCM 11910P, and heat-treated *Limosilactobacillus fermentum* LM1020 were added were calculated. Then, the effect of heat-treated lactic acid bacteria on the promotion of growth of dermal papilla cells was calculated using the formula below and compared. All the tests were repeated three times, and the average of each result was calculated and compared.

Dermal papilla cell growth promotion effect (%)=(B−A) ÷A×100

A=Growth rate of dermal papilla cells in non-treatment group

B=Growth rate of dermal papilla cells when treated with heat-treated lactic acid bacteria As a result, the heat-treated *Limosilactobacillus fermentum* KCCM 11910P at a concentration of $2.5 \times 10^7$ cells/mL inhibited the growth of dermal papilla cells, and the heat-treated *Lacticaseibacillus paracasei* KCTC 14004BP promoted the growth of dermal papilla cells but exhibited a cell growth rate that was more than two times lower than that of the heat-treated *Limosilactobacillus fermentum* LM1020 of the present disclosure.

Example 4. Effect of Proliferating Dermal Papilla Cells Depending on Concentration of Heat-Treated *Limosilactobacillus fermentum* LM1020

It was confirmed whether the heat-treated *Limosilactobacillus fermentum* LM1020, which had the best effect of promoting the growth of dermal papilla cells in Examples 1 and 2, can promote the proliferation of dermal papilla cells even in situations where growth factors are insufficient. After dermal papilla cells were seeded in a 96-well plate and cultured for 24 hours, the medium in the well was replaced with a medium lacking growth factor and further cultured for 24 hours. Then, the heat-treated *Limosilactobacillus fermentum* LM1020 was added at different concentrations, and 24 hours later, it was checked whether it can promote the growth of dermal papilla cells. The dermal papilla cell growth promotion effect was confirmed by dissolving formazan prepared by adding 0.5 mg/mL of thiazolyl blue tetrazolium bromide (MTT) and culturing at 37° C. in DMSO and measuring the absorbance at 570 nm.

Figure 3:
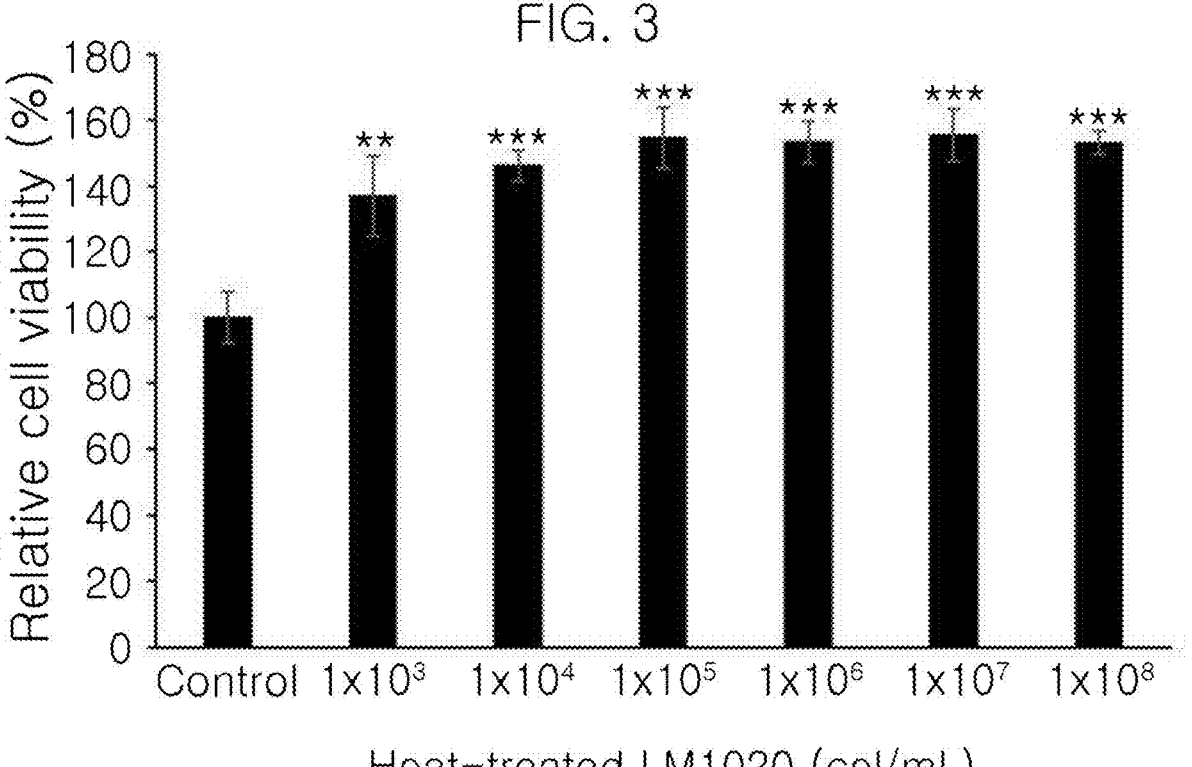
FIG. 3 shows the result of comparing the effect of heat-treated *Limosilactobacillus fermentum* LM1020 on the proliferation of dermal papilla cells depending on the concentration of the heat-treated *Limosilactobacillus fermentum* LM1020.

As a result, the heat-treated *Limosilactobacillus fermentum* LM1020 proliferated dermal papilla cells even under culture conditions lacking dermal papilla cell growth factors, and the growth rate of dermal papilla cells increased in a concentration-dependent manner in a concentration range of from $1 \times 10^3$ cells/mL to $1 \times 10^5$ cells/mL. Also, the dermal papilla cell proliferation effect was similar regardless of the concentration at a high concentration of $1 \times 10^6$ cells/mL or higher. It was confirmed that the dermal papilla cell proliferation promotion effect was highest at $1 \times 10^7$ cells/mL and was 156% higher than that of the non-treatment group (FIG. 3).

Example 5. Increase in Expression Levels of Proteins Related to Proliferation of Dermal Papilla Cells To identify the mechanism by which the heat-treated *Limosilactobacillus fermentum* LM1020, which had the best effect of promoting the growth of dermal papilla cells in Examples 1 and 2, promotes the proliferation of dermal papilla cells, the expression levels of proteins related to the proliferation of dermal papilla cells were measured.

Dermal papilla cells are mesoderm-derived fibroblasts, and the proliferation of dermal papilla cells is regulated by cell cycle proteins, such as cyclins, CDKs (cyclin-dependent kinases), and CDK inhibitors. Cells exist in a resting or proliferating phase, and a growing cell goes through the cell cycle of G1 phase, S phase, which is the DNA synthesis phase, G2 phase, and M phase where mitosis occurs, and finally divides into two cyst cells and proliferates.

Cyclin-dependent kinase 2 (CDK2), which is a kinase involved in regulation of cell cycle, is essential for meiosis, but is not required for mitosis. It regulates the activation of cyclin BCDK1 as a mechanism to control the timing of entering mitosis and meiosis by controlling the subsequent activation of cyclin B/CDK1 by phosphorylation. CDK2 activity is maximally expressed during the S phase and the G2 phase of cell division. Cyclin-dependent kinase 4 (CDK4) is required for cell cycle transition from the G1 phase to the S phase. Cyclin-dependent kinase 6 (CDK6) promotes the G1/S transition and is involved in cell cycle initiation and maintenance during cell division. The main function of CDK6 is to prevent cell proliferation and regulate negative cell division. Cyclin B1 is a regulatory protein involved in mitosis as well as a cell cycle regulatory transcript expressed during the G2/M phases of the cell cycle.

Cyclin B1 serves to determine mitosis of cells, and after being activated to form a cyclin B1-CDK1 complex, it promotes early mitosis through various mechanisms.

Cyclin D1 is one of target genes of the Wnt/β-catenin signaling pathway, which plays an important role in processes, such as hair growth, stem cell regulation, and cell proliferation, and affects the cell division throughout the cell division cycle of dermal papilla cells.

Cyclin E1 can induce the early G1 phase of the cell division cycle of dermal papilla cells. Cyclin E1 promotes the transition from the G1 phase to the S phase and induces the initiation of DNA synthesis. Cyclin E1 is maximally expressed during the G1/S phases of the cell cycle.

To measure the protein expression level of dermal papilla cells, dermal papilla cells were seeded in a 6-well microplate at a concentration of $4\times10^5$ cells/mL and then cultured for 24 hours. The dermal papilla cell culture medium was replaced with a basal medium (from which dermal papilla cell growth factors, such as insulin, were removed) and then further cultured for 24 hours. Then, the dermal papilla cell culture medium was replaced with a medium treated the heat-treated *Limosilactobacillus fermentum* LM1020 at different concentrations (final concentrations: $1\times10^6$ cells/mL, $1\times10^7$ cells/mL, and $1\times10^8$ cells/mL of the heat-treated *Limosilactoba-*

*cillus fermentum* LM1020). While dermal papilla cells were cultured together with the heat-treated *Limosilactobacillus fermentum* LM1020 at different concentrations for 24 hours, the proliferation of dermal papilla cells was induced. After the completion of culturing, proteins of the dermal papilla cells were extracted by using a Pro-Prep™ lysis buffer (Intron, Korea). The amount of the extracted proteins was measured by BCA protein assay, and the protein expression level was measured by Western blotting with a Protein Simple Jess system (Jess; Protein Simple, USA). Electrophoresis, blocking, primary antibody reaction, and secondary antibody reaction were induced inside the capillary by using a Jess capillary cartridge, and the expression level was checked by using an ECL detection reagent.

As a result, it was confirmed that the heat-treated *Limosilactobacillus fermentum* LM1020 grows dermal papilla cells by increasing the expression of cyclin and CDK proteins necessary for the growth cycle of dermal papilla cells (FIG. 4A to FIG. 4F). The expression levels of proteins which affect the proliferation of dermal papilla cell dermal papilla cells varied depending on the concentration of the heat-treated *Limosilactobacillus fermentum* LM1020, but the expression of CDK2, CDK4, cyclin B1, and cyclin D1 tended to increase, while the expression of CDK6 and cyclin E1 tended to decrease (Table 2).

Figure 4A:
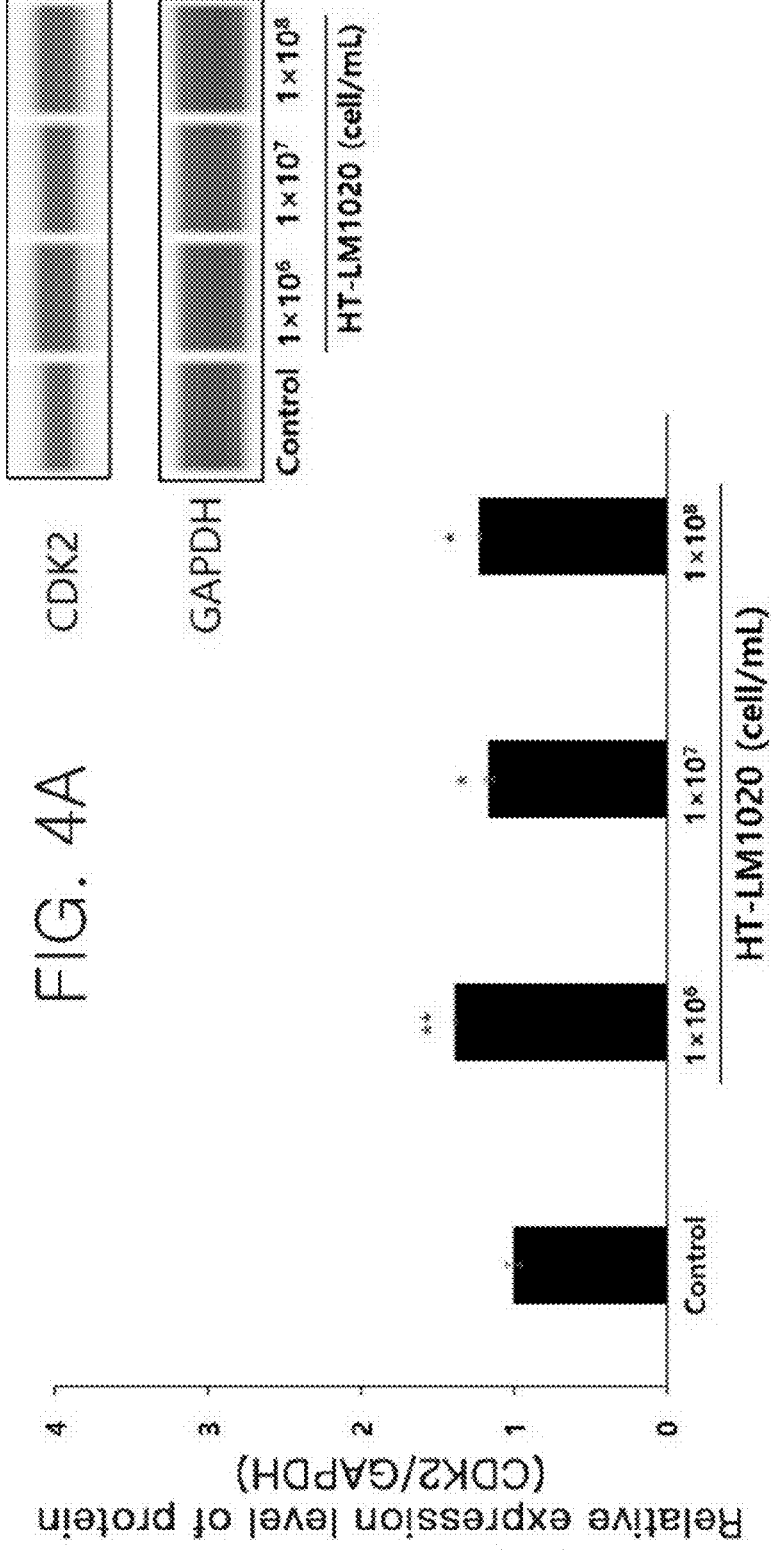
FIG. 4A shows the changes in expression level of CDK2 in dermal papilla cells after treatment with heat-treated *Limosilactobacillus fermentum* LM1020.
Figure 4C:
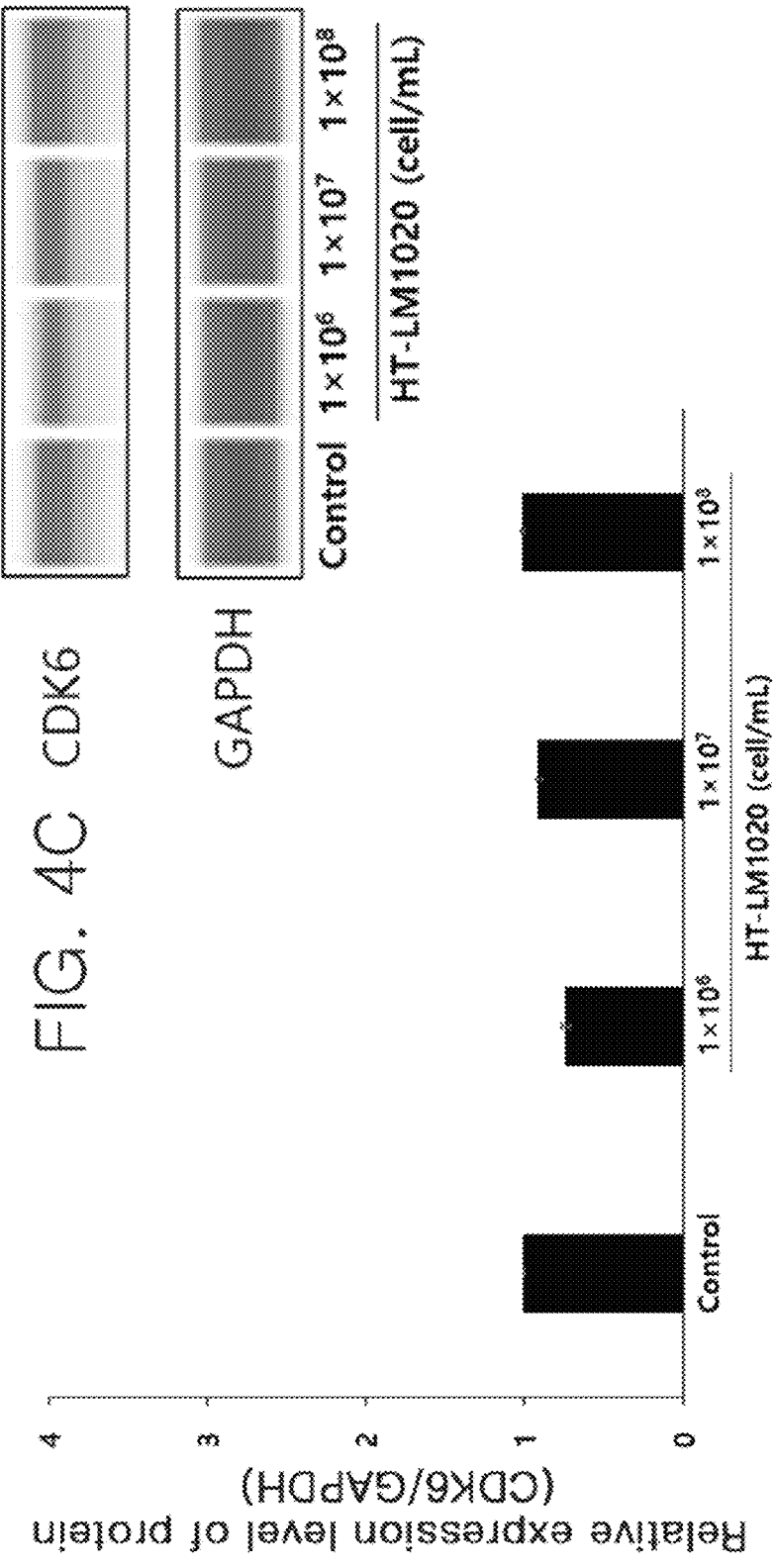
FIG. 4C shows the changes in expression level of CDK6 in dermal papilla cells after treatment with heat-treated *Limosilactobacillus fermentum* LM1020.
Figure 4D:
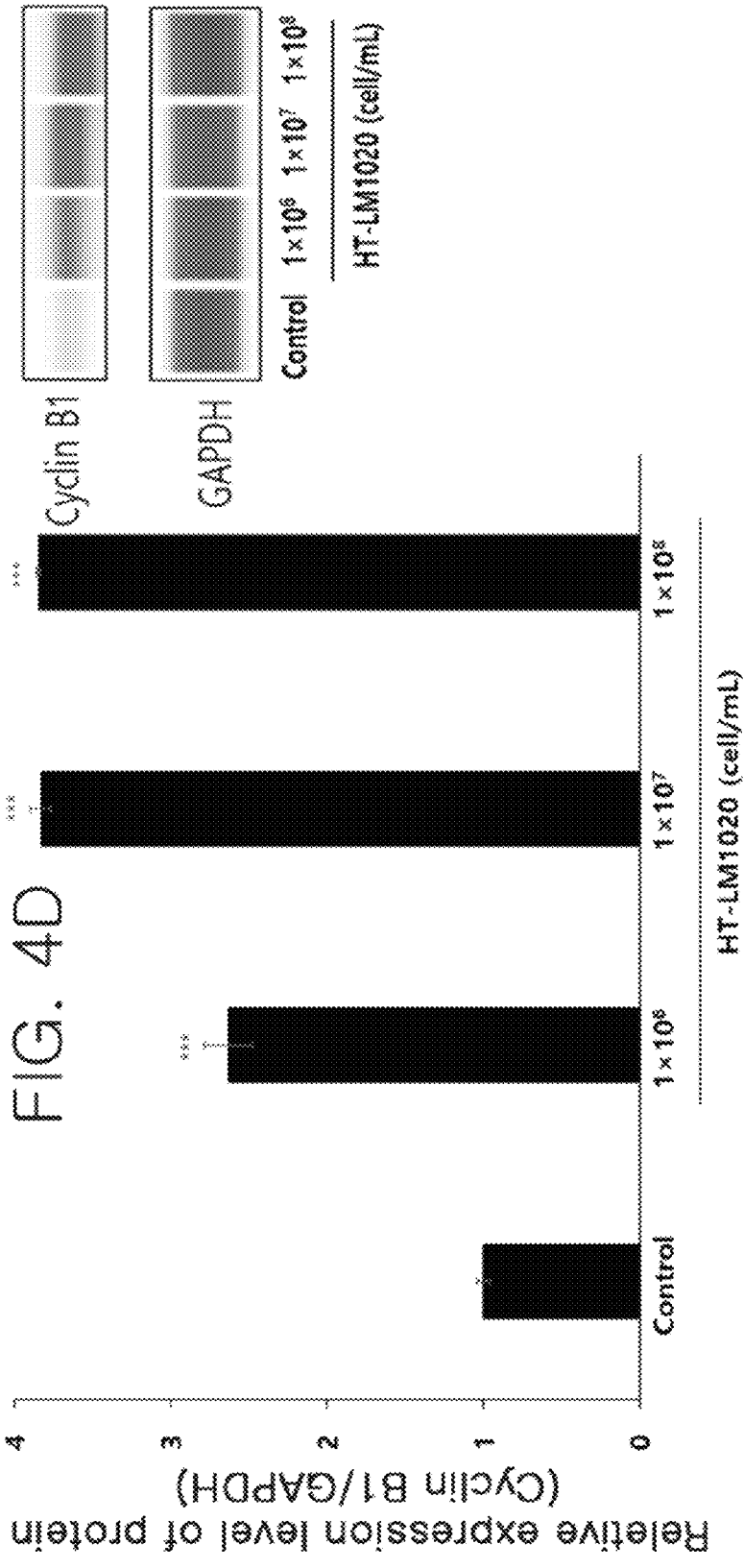
FIG. 4D shows the changes in expression level of cyclin B1 in dermal papilla cells after treatment with heat-treated *Limosilactobacillus fermentum* LM1020.

In particular, the heat-treated *Limosilactobacillus fermentum* LM1020 increased the expression level of cyclin B1 by up to 3.9-fold (FIG. 4D). This means that the number of cells reaching the G2/M phases of the cell division of dermal papilla cells was higher than that of the control group (untreated) during the same growth time and the number of dermal papilla cells undergoing division after DNA replication increased.

Figure 4E:
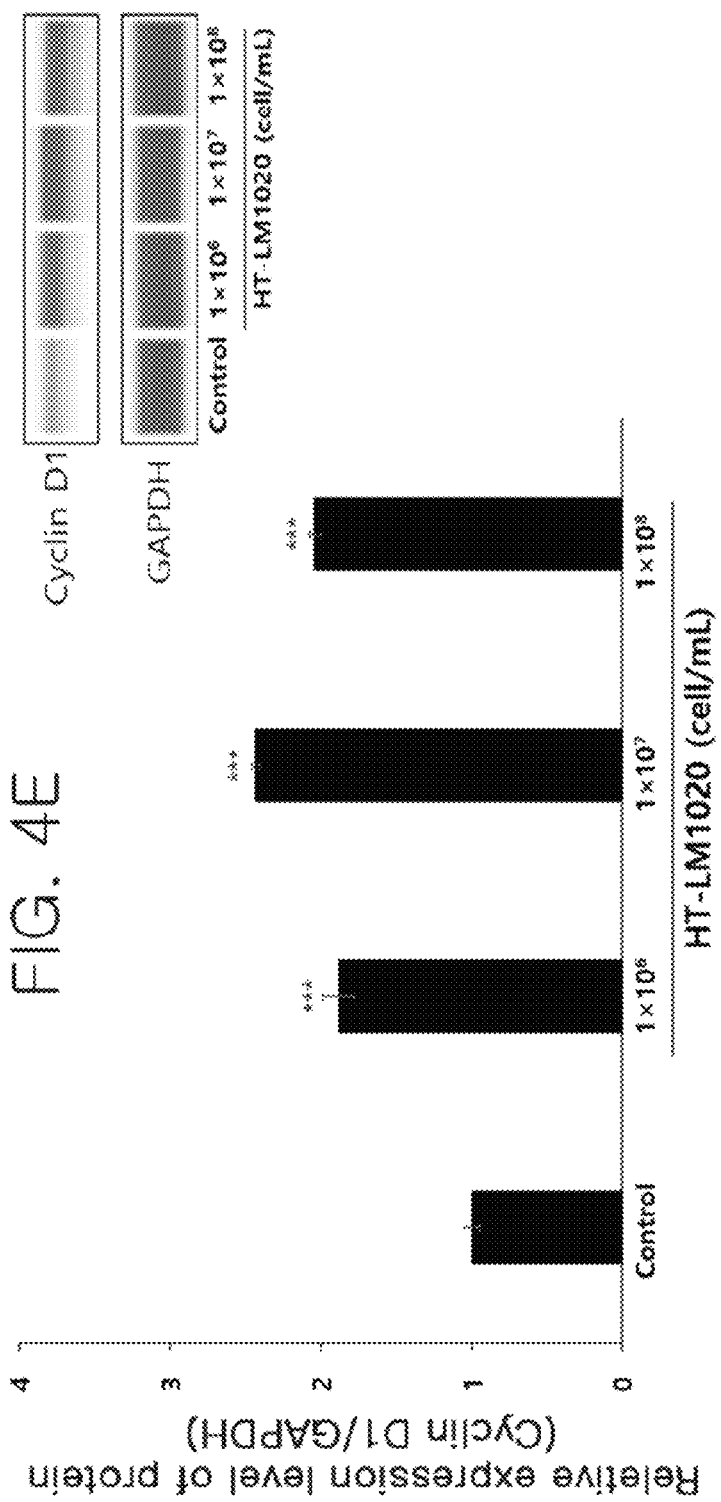
FIG. 4E shows the changes in expression level of cyclin D1 in dermal papilla cells after treatment with heat-treated *Limosilactobacillus fermentum* LM1020.

Also, when dermal papilla cells were treated with the heat-treated *Limosilactobacillus fermentum* LM1020, the expression of cyclin D1 protein which affects the cell division throughout the cell division cycle of dermal papilla cells increased by up to 2.4-fold (FIG. 4E). This means that the heat-treated *Limosilactobacillus fermentum* LM1020 promoted the growth of the dermal papilla cells by forming a cyclin D1-CDK4 complex in the dermal papilla cells and inducing the transition from the G1 phase of the cell division to the S phase where DNA is replicated.

Figure 4F:
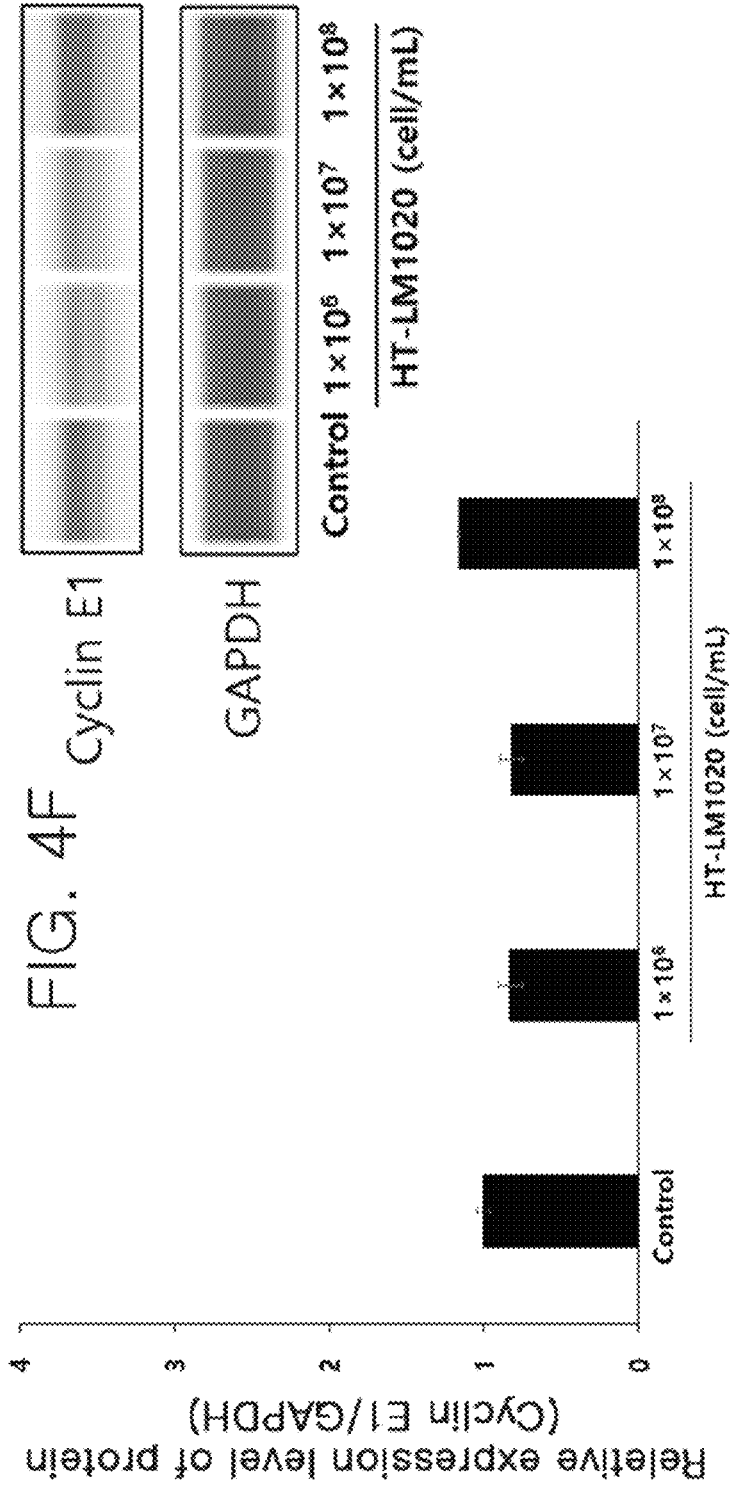
FIG. 4F shows the changes in expression level of cyclin E1 in dermal papilla cells after treatment with heat-treated *Limosilactobacillus fermentum* LM1020.
Figure 5A:
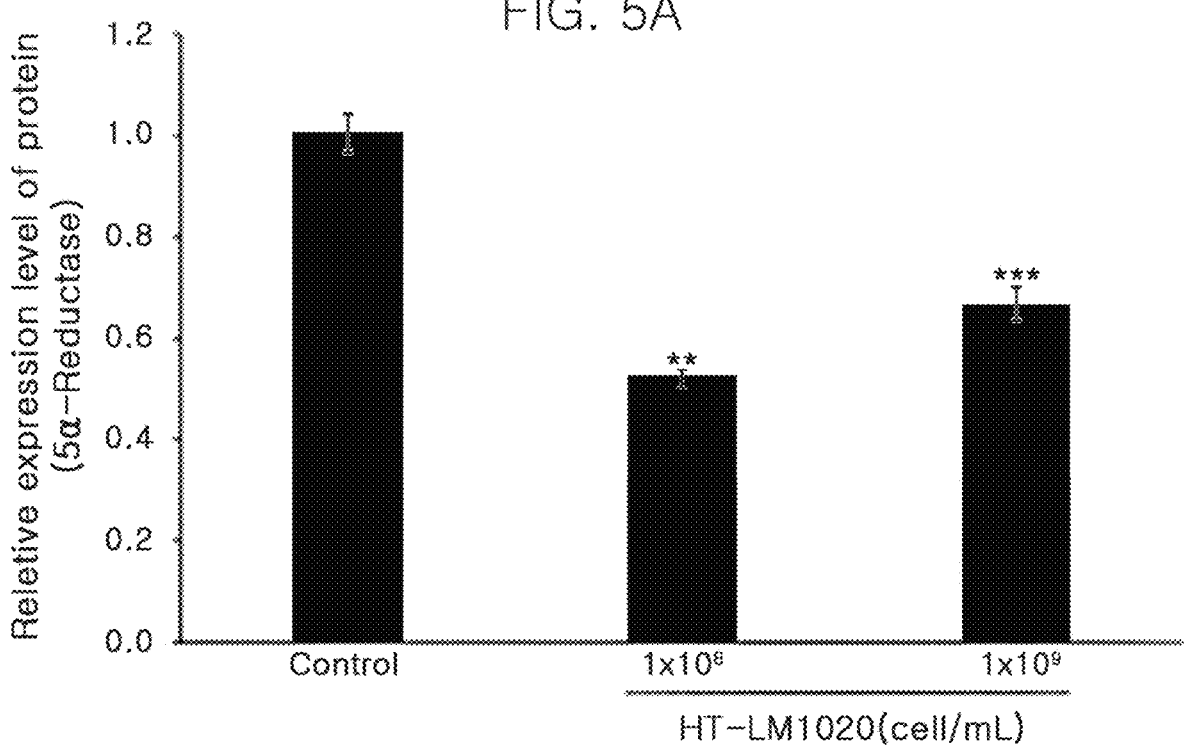
FIG. 5A shows the result of verifying 5α-reductase expression levels of heat-treated *Limosilactobacillus fermentum* LM1020 in human scalp tissue.
Figure 5B:
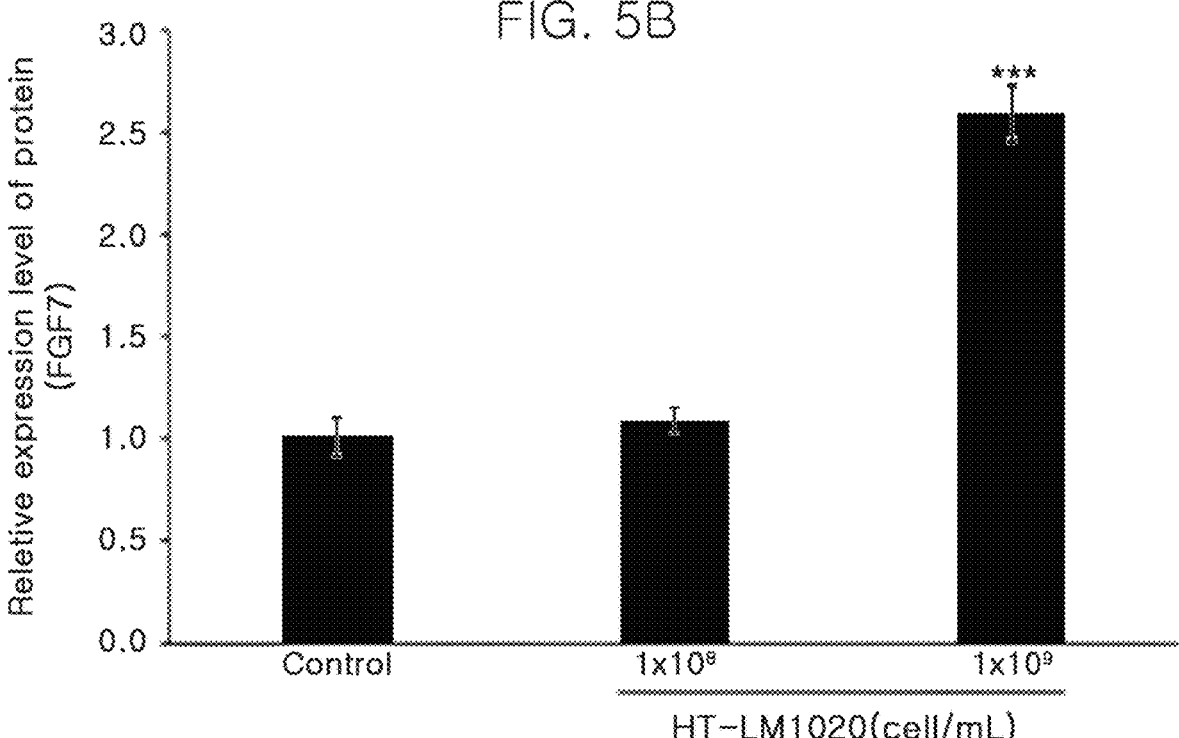
FIG. 5B shows the result of verifying FGF7 (fibroblast growth factor 7) expression levels of heat-treated *Limosilactobacillus fermentum* LM1020 in human scalp tissue.
Figure 5C:
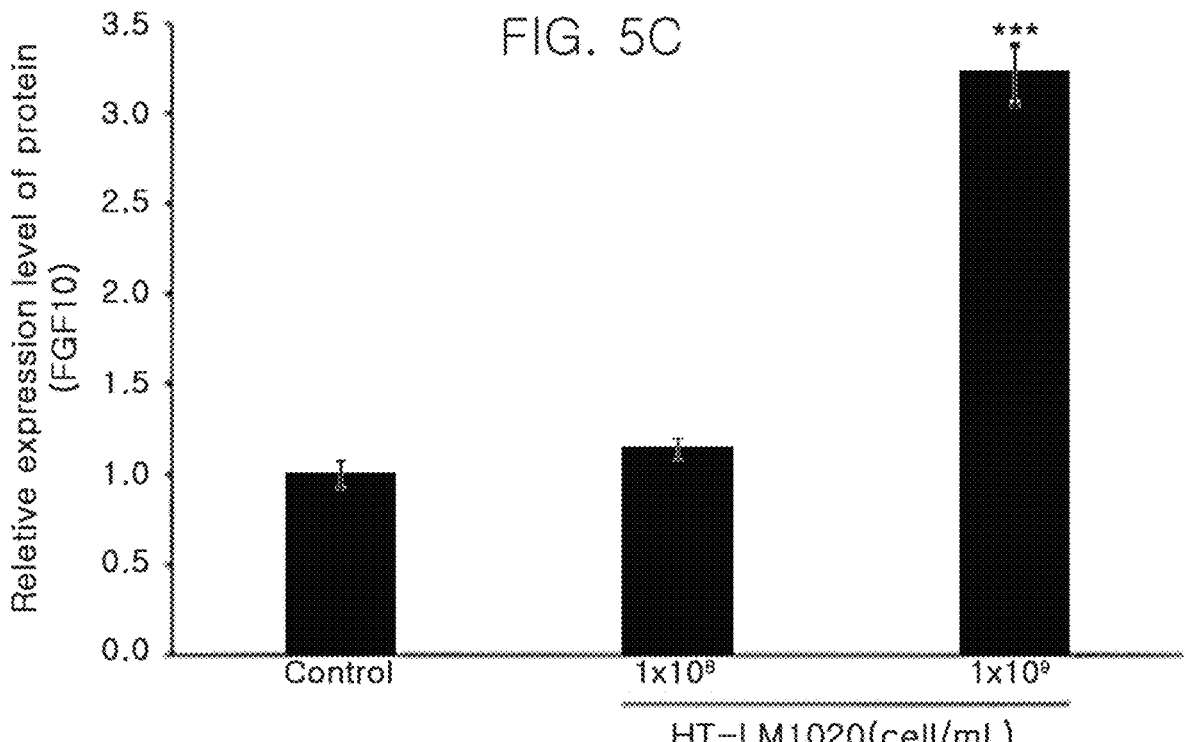
FIG. 5C shows the result of verifying FGF10 (fibroblast growth factor 10) expression levels of heat-treated *Limosilactobacillus fermentum* LM1020 in human scalp tissue.
Figure 5D:
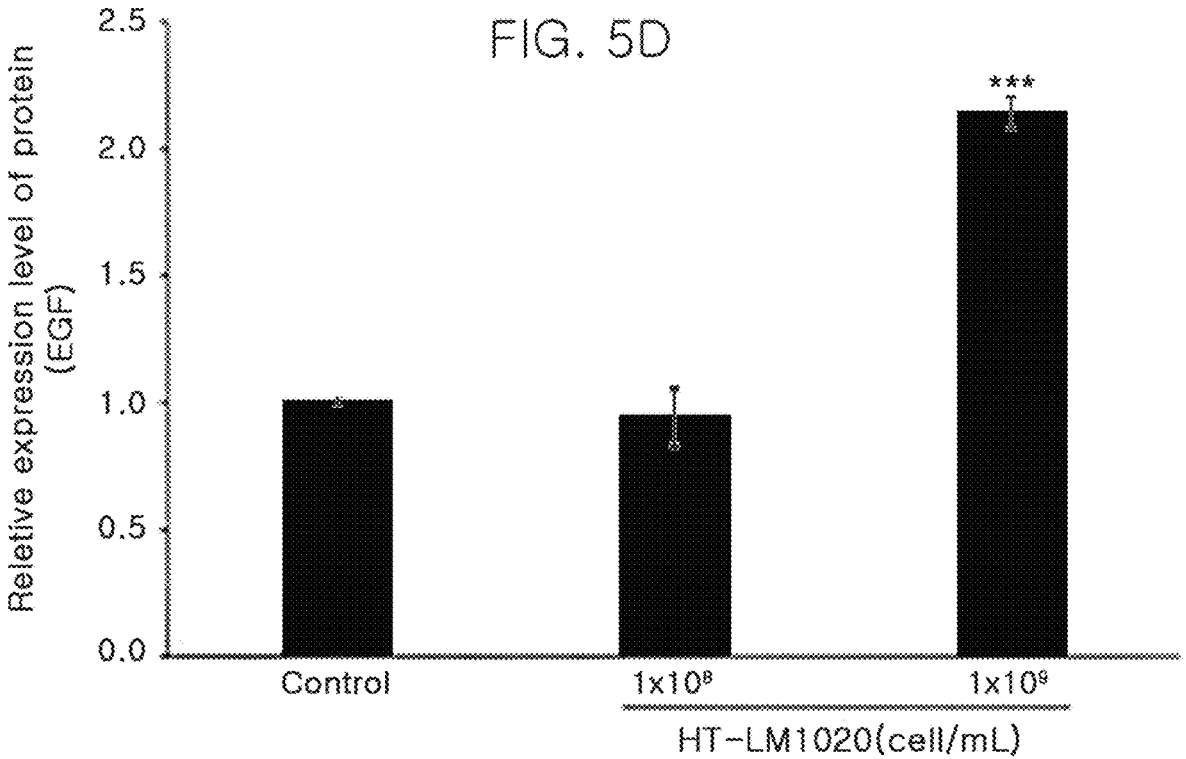
FIG. 5D shows the result of verifying EGF (epidermal growth factor) expression levels of heat-treated *Limosilactobacillus fermentum* LM1020 in human scalp tissue.
Figure 6:
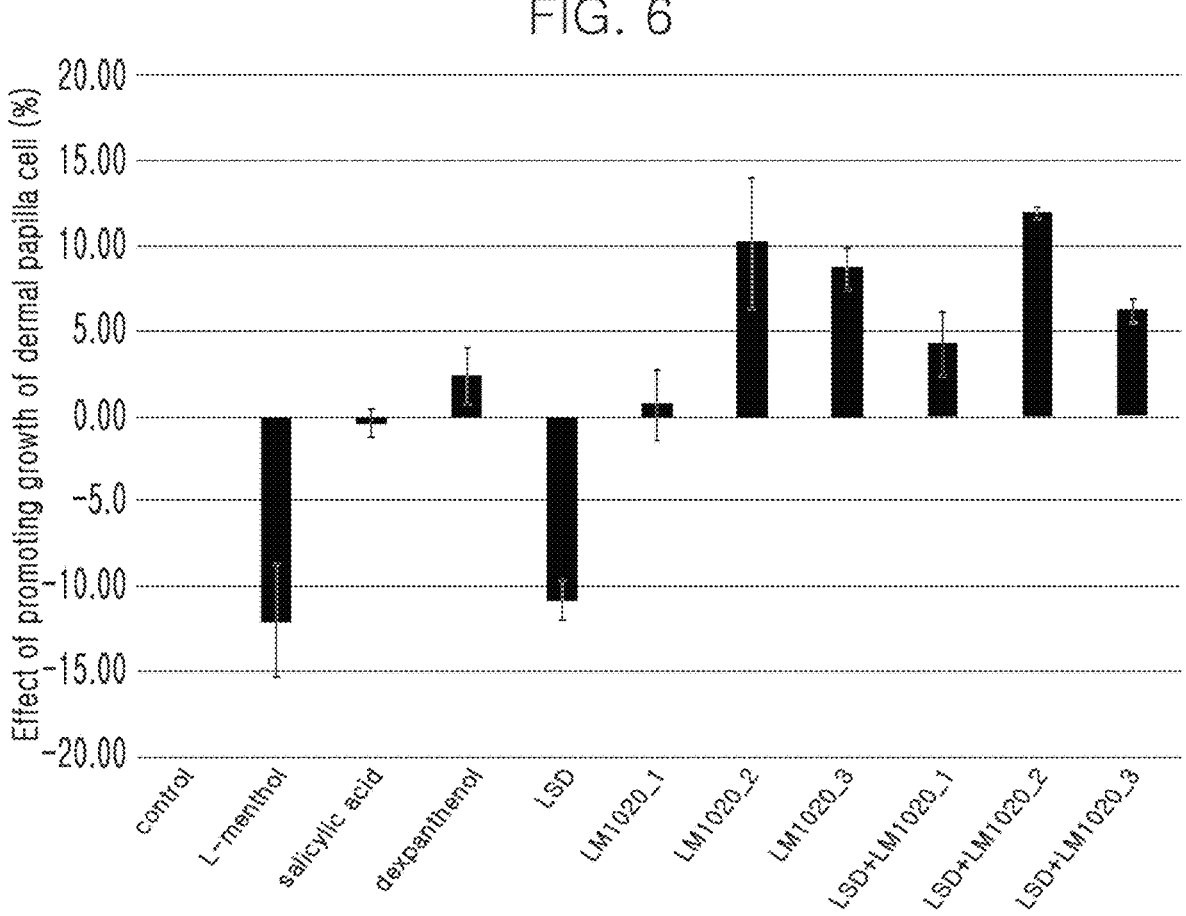
FIG. 6 shows the result of comparing the effect of L-menthol, salicylic acid, dexpanthenol, mixtures thereof (LSD), heat-treated *Limosilactobacillus fermentum* LM1020, and compounds of heat-treated *Limosilactobacillus fermentum* LM1020 with L-menthol, salicylic acid and dexpanthenol on the promotion of growth of dermal papilla cells.

Meanwhile, after the treatment with the heat-treated *Limosilactobacillus fermentum* LM1020, the expression levels of cyclin E and CDK6, which induce the early G1 phase of the cell division cycle of dermal papilla cells, were slightly reduced or maintained at similar levels to before the treatment (FIG. 4C and FIG. 4F). This means that more dermal papilla cells treated with the heat-treated *Limosilactobacillus fermentum* LM1020 passed the G1 phase, which is the initial stage of the cell division cycle and reached the G2/M phases.

TABLE 2

| L. fermentum | Increase in protein expression level of test group compared to control group | | | | | |
|---|---|---|---|---|---|---|
| LM1016 Throughput | CDK2 | CDK4 | CDK6 | Cyclin B1 | Cyclin D1 | Cyclin E1 |
| $1 \times 10^6$ cell/mL | 1.38-fold | 1.40-fold | 0.74-fold | 2.63-fold | 1.88-fold | 0.83-fold |
| $1 \times 10^7$ cell/mL | 1.16-fold | 2.07-fold | 0.91-fold | 3.83-fold | 2.43-fold | 0.82-fold |
| $1 \times 10^7$ cell/mL | 1.22-fold | 1.56-fold | 1.01-fold | 3.85-fold | 2.04-fold | 1.16-fold |

Example 6. Measurement of Hair Loss Prevention and Hair Growth Effect by Using Human-Derived Tissue 6-1) Culture of Explant Tissue Human scalp tissue provided for research purposes (IRB No. 4-2021-1524; Yonsei University College of Medicine, Severance Medical Center Bioethics Committee) was washed several times with PBS to remove residual impurities and then prepared into 1 cm×1 cm.

The heat-treated *Limosilactobacillus fermentum* LM1020 was diluted to a concentration of $1×10^8$ cells/mL or $1×10^9$ cells/mL in a scalp tissue-dedicated medium and then, 50 μL was applied to the human scalp tissue. A negative control group was applied with 50 μL of the scalp tissue-dedicated medium instead of the heat-treated *Limosilactobacillus fermentum* LM1020. Culturing was performed in the dedicated medium at 37° C. with 5% $CO_2$ conditions, and the dedicated medium was replaced, and treatment materials were applied at intervals of 24 hours. After 72 hours from the application, subcutaneous tissue, epidermal tissue, and dermal tissue were separated from each tissue and used for test.

6-2) Real-Time Polymerase Chain Reaction (RT-PCR)

The gene expression levels of hair loss- and hair growth-related factors (5α-reductase-1, FGF7, FGF10 and EGF) were measured through RT-PCR. The gene expression level of 5α-reductase-1 was measured from the subcutaneous tissue separated from the human scalp tissue, and the gene expression levels of FGF7, FGF10, and EGF were measured from the epidermal and dermal tissues.

Specifically, 5α-reductase-1, which is one of the hair loss-related factors, is an enzyme mainly distributed in dermal papilla cells, sebaceous glands, epidermis, and keratinocytes of hair follicles, and reacts with testosterone to produce DHT (dihydrotestosterone), which is the main cause of hair loss. It is known that a decrease in gene expression of 5α-reductase-1 in human dermal papilla cells is involved in preventing hair loss (H Rastegar et al., 2015).

Fibroblast growth factor 7 (FGF7) is produced by fibroblasts and secreted into keratinocytes. It is a proliferation factor that promotes the proliferation of epithelial and epidermal cells. FGF7 is known to promote hair follicle cell division, induce the proliferation of the vascular system of the dermal papilla, and increase the amount of extracellular matrix to maintain hair follicles in the growth phase. Fibroblast growth factor 10 (FGF10) is a factor that contributes to initial cell formation by inducing resting hair follicles to be in the growth or proliferation phase and promotes hair growth (Sole Cho et al., 2016).

EGF is well known as a growth factor involved in hair follicle maturation and has been researched to promote the proliferation of dermal papilla cells through activation of the Notch mechanism (Zhang et al., 2016).

After the tested tissue was pulverized using a TissueLyser II (Qiagen), total RNA was extracted using a TRIzol Reagent (Invitrogen) and the extracted total RNA was extracted to synthesize cDNA by using RNA to cDNA EcoDry™ Premix (Oligo dT) (Clontech). The synthesized cDNA, a Taqman Fast Advanced Master Mix (Applied Biosystems) and Taqman primers for each target (SRD5A1 (5-α-reductase-1): Hs00971645_g1, FGF7: Hs00940253_m1, FGF10: Hs00610298_m1, EGF: Hs01100002_m1; Applied Biosystems) were used to induce RT-PCR. A GAPDH (Hs02786624_g1, Applied Biosystems), which is a housekeeping gene, was used for relative quantitative analysis of each gene.

When cDNA was amplified, the amount of amplification was measured in real time to obtain a threshold cycle ($C_T$) value, which is the intersection between an amplification curve and a threshold line, and a relative quantification value (RQ) was obtained based on the $C_T$ value to confirm a relative mRNA expression level of a target gene. The RQ was calculated using the formula below.

Treatment (Test Group): Treatment with test product

Control (Control Group): Negative control group

Target gene: SRD5A1 (5α-reductase-1), FGF7, FGF10, and EGF

Housekeeping gene: GAPDH 6-3) Statistical Analysis

Statistical analysis was verified using the IBM SPSS statistics 25.0 program, and the significance of the control group was confirmed with a hypothesized mean difference of 5% ($p<0.05$). After a normality test, the significance was confirmed through an independent sample T-test (parametric method) depending on whether normality was met.

6-4) Research Result

5α-reductase, which is known to cause hair loss, was significantly decreased at all concentrations regardless of the concentration of the heat-treated *Limosilactobacillus fermentum* LM1020 ($p<0.05$). FGF7, FGF10, and EGF, which induce hair growth, were significantly increased in the treatment group with a high concentration of $1×10^9$ cells/mL ($p<0.05$). Therefore, it was confirmed that the heat-treated *Limosilactobacillus fermentum* LM1020 can help prevent hair loss and promote hair growth.

Example 7. Functional Raw Materials Helping Relieve Hair Loss Symptoms and Hair Loss Prevention Effect of Heat-Treated *Limosilactobacillus fermentum* LM1020

The effect on the growth of dermal papilla cells was confirmed when the heat-treated *Limosilactobacillus fermentum* LM1020 was used together with L-menthol, salicylic acid, and dexpanthenol, which are active ingredients frequently used for functional cosmetics that help relieve hair loss symptoms. After the dermal papilla cells were seeded in a 96-well plate and cultured for 24 hours, the medium in the well was replaced with a medium lacking growth factor and further cultured for 24 hours. Then, the heat-treated *Limosilactobacillus fermentum* LM1020, L-menthol, salicylic acid, and dexpanthenol were used alone or mixed in a ratio of 3:2.6:2 and used for treatment of dermal papilla cells prepared by the above-described method to determine the effect on the growth of the dermal papilla cells.

A growth rate of dermal papilla cells when cultured alone and growth rates of dermal papilla cells when treated alone or in a combination of L-menthol, salicylic acid, dexpanthenol, and the heat-treated *Limosilactobacillus fermentum* LM1020 were calculated. Then, the effects of the respective treatment materials on the promotion of growth of dermal papilla cells were calculated using the formula below and compared with each other. All the tests were repeated three times, and the average of each result was calculated and compared.

Dermal papilla cell growth promotion effect $(\%)=(B−A)÷A×100$

A=Growth rate of dermal papilla cells in non-treatment group

B=Growth rate of dermal papilla cells when treated with L-menthol, salicylic acid, dexpanthenol, and heat-treated *Limosilactobacillus fermentum* LM1020

As a result, among L-menthol, salicylic acid, and dexpanthenol, which are widely known to have hair loss relief effect, L-menthol and salicylic acid were found to inhibit the growth of dermal papilla cells. Dexpanthenol was able to promote the growth of dermal papilla cells, but its effect on the promotion of growth of dermal papilla cells was lower than that of the heat-treated *Limosilactobacillus fermentum* LM1020 at all concentrations. Meanwhile, it was confirmed that when the heat-treated *Limosilactobacillus fermentum* LM1020 is used for treatment together with compounds of L-menthol, salicylic acid, and dexpanthenol, it is possible to overcome the effect of the compounds on the inhibition of growth of dermal papilla cells and promote the growth of dermal papilla cells. In order to thoroughly understand their synergistic effect, the effect to be predicted was calculated using the Colby formula, and a prediction value was compared with an experimental value (measurement value) to verify whether a synergistic effect exceeding the prediction value can be achieved.

Colby Formula $$\text{Prediction value} = (A + B) - (A \times B/100)$$

(Source)

As a result, a mixture of L-menthol, salicylic acid, and dexpanthenol in a ratio of 3:2.6:2 inhibited the growth of dermal papilla cells, but when the mixture was used for treatment together with the heat-treated *Limosilactobacillus fermentum* LM1020, the growth of dermal papilla cells was promoted. Also, when dermal papilla cells were treated with the mixture and the heat-treated *Limosilactobacillus fermentum* LM1020 at a concentration of $1\times10^6$ cells/mL or $1\times10^7$ cells/mL, the dermal papilla cell growth promotion effect was greater than when dermal papilla cells were treated with the heat-treated *Limosilactobacillus fermentum* LM1020 alone.

TABLE 3

| | | Effect of promoting growth of dermal papilla cell (%) | |
| No. | Name | Measured value | Predicted value[1] |
| --- | --- | --- | --- |
| 1 | Control group (no additives) | 0 | 0 |
| 2 | L-menthol | −12.05 ± 3.31 | — |
| 3 | salicylic acid | −0.39 ± 0.80 | — |
| 4 | dexpanthenol | 2.35 ± 1.61 | — |
| 5 | LSD (L-menthol:salicylic acid:dexpanthenol 3:2.5:2 mixture) | −10.81 ± 1.17 | — |
| 6 | LM1020_1 (heat-treated *Limosilactobacillus fermentum* LM1020 dead cell 1 × 10⁶ cell/mL) | 0.69 ± 2.01 | — |
| 7 | LM1020_2 (heat-treated *Limosilactobacillus fermentum* LM1020 dead cell 1 × 10⁷ cell/mL) | 10.17 ± 3.85 | — |
| 8 | LM1020_3 (heat-treated *Limosilactobacillus fermentum* LM1020 dead cell 1 × 10⁸ cell/mL) | 8.66 ± 1.22 | — |
| 9 | LSD + LM1020_1 | 4.27 ± 1.88 | −10.045 |
| 10 | LSD + LM1020_2 | 11.96 ± 0.34 | 0.459 |
| 11 | LSD + LM1020_3 | 6.21 ± 0.71 | −1.2134 |

1) Prediction value calculation formula=Prediction value calculated by Colby formula

Preparation Example 1. Development of Liquid Formulation Containing Heat-Treated *Limosilactobacillus fermentum* LM1020

A liquid formulation that can be evenly sprayed and applied to the scalp was developed. The liquid formulation contains L-menthol, salicylic acid, dexpanthenol, and the heat-treated *Limosilactobacillus fermentum* LM1020 whose synergistic effect was confirmed in Example 5 and which are active ingredients of functional cosmetics for relieving hair loss. The developed liquid formulation contains L-menthol 0.3%, salicylic acid 0.26%, dexpanthenol 0.2%, heat-treated *Limosilactobacillus fermentum* LM1020 5%, and further contains purified water, ethanol, alanine/histidine/lysine polypeptide copper (HCL), polyacrylate crosspolymer-6, coconut acid, proline, tea tree oil, glycerin, peptide, butylene glycol, 1,2-hexanediol, green tea extracts, lavender flower extracts, quince extracts, and ethyl hexanediol.

Example 8. Verification of Hair Loss Relief Effect Through Human Application Test A human application test was conducted by Global Medical Research Center Co., Ltd., and the human application test was approved by Research Ethics Committee (Approval Number: GIRB-21029-ET). The test participants were 25 Korean men and women aged 18 to 54, and two of them dropped out.

All the participants applied the product of Preparation Example 1 evenly to the scalp before going to bed for 6 months, and visited the center at intervals of 0, 8, 16, and 24 weeks to evaluate compliance with product usage, measure a hair density using a phototrichogram, and perform a visual evaluation by experts and a participant effectiveness survey (satisfaction with hair growth, satisfaction with hair loss relief, and satisfaction with frontal hairline).

As a result of investigating the test participants' compliance with product usage, it was confirmed that the number of test participants with less than 80% usage based on the number of uses was "0". Therefore, all the participants used the test product once a day during the 24-week test period by applying it to the scalp before going to bed as specified.

The efficacy of the test product was verified through hair density measurement (phototricogram), photography and visual evaluation by experts, and effectiveness evaluation on satisfaction with usage. To measure a hair density, a hair loss area to be evaluated was shaved in a circle of 1 cm², then a dot with a diameter of 1 mm was tattooed and photographed using a hair density meter. The hair density was measured every 8 weeks, a total of 4 times, and the number of strands of hair within the circle of 1 cm² based on the tattoo was measured.

As a result, the test participants' hair densities continued to increase compared to before using the test product, and after 16 weeks, the hair densities increased statistically significantly compared to before use ($p<0.05$).

TABLE 4

| | Period of use | Test group | Change in hair density(n/cm$^2$) |
|---|---|---|---|
| hair density (n/cm$^2$) | 0 week | 133.696 ± 24.697 | |
| | 8th week | 137.739 ± 24.588 | 4.043 |
| | 16th week | 139.609 ± 24.954 | 5.913 |
| | 24th week | 140.870 ± 24.781 | 7.174 |
| p-value of | 8th week | 1.000 | |
| comparison between | 16th week | 0.019 | |
| groups | 24th week | 0.002 | |

The visual evaluation by experts was conducted by photographing the test areas, i.e., the crown of the head (90°) and the frontal hairline (45°). The visual evaluation was conducted by two experts, and changes were evaluated on a 7-point scale. As a result, the test participants could visually recognize the relief of hair loss symptoms and the growth of hair while using the test product. As a result of verifying the precision of the research result by checking the degree of agreement in visual evaluation between the researchers using the Intraclass Correlation Coefficients (ICC), the correlation coefficient for visual evaluation between the researchers was 0.916, which was close to 1, indicating perfect agreement.

TABLE 5

| | | Test group | |
|---|---|---|---|
| | Period of use | Participant 1 | Participant 2 |
| Evaluation score by | 0 week | 0.000 ± 0.000 | 0.000 ± 0.000 |
| eyes | 8th week | 0.043 ± 0.209 | 0.087 ± 0.288 |
| | 16th week | 0.261 ± 0.541 | 0.261 ± 0.541 |
| | 24th week | 0.261 ± 0.541 | 0.217 ± 0.518 |

After using the product, the test participant effectiveness survey was conducted on a 7-point scale (−3: very worse, −2: worse, −1: slightly worse, 0: no change, 1: slightly better, 2: improved, 3: very improved). As a result, the participants who used the test product for a total of 24 weeks were satisfied with hair growth, hair loss relief, and frontal hairline, and satisfaction tended to increase as the period of usage increased.

TABLE 6

| | Period of use | Test group |
|---|---|---|
| Satisfaction with | 8th week | 0.913 ± 0.848 |
| hair growth | 16th week | 1.435 ± 0.788 |
| | 24th week | 1.271 ± 0.600 |

TABLE 7

| | Period of use | Test group |
|---|---|---|
| Satisfaction with | 8th week | 1.174 ± 0.778 |
| hair loss relief | 16th week | 1.304 ± 0.703 |
| | 24th week | 1.522 ± 0.730 |

TABLE 8

| | Period of use | Test group |
|---|---|---|
| Satisfaction with | 8th week | 0.609 ± 0.783 |
| frontal hair line | 16th week | 1.217 ± 0.795 |
| | 24th week | 1.217 ± 0.902 |

Example 9. Changes in Microbial Environment of Scalp Before and After Use of Product Containing Heat-Treated *Limosilactobacillus fermentum* LM1020

The microbial environment of the scalp before use of the product of Preparation Example 1 was compared with the microbial environment of the scalp after 24 weeks of the usage. The scalp microorganisms were collected by using sterilized skin-microbiome collection swabs, and immediately after collection, the samples were maintained at a low temperature using a nucleic acid transport medium and sent to a microbiome analysis institute. The scalp microorganisms were analyzed by preparing a library after sequencing and performing comparison through 16S metagenome analysis.

As a result, the test participants had a four-fold increase in scalp lactic acid bacteria after using the product of Preparation Example 1 (FIG. 7A). Also, the microbial diversity of the scalp was also improved. The total microbial diversity of the scalp increased by 60% (FIG. 7B), and the lactic acid bacteria diversity of the scalp of the scalp increased by 176% (FIG. 7C). After the use of the product of Preparation Example 1, *Staphylococcus caprae*, a microorganism that decreases in people with alopecia aerata, tended to increase (FIG. 7D and FIG. 7E). Therefore, it was confirmed that when the heat-treated *Limosilactobacillus fermentum* LM1020 is applied to the scalp, it can prevent hair loss symptoms by changing the microbial environment of the scalp.

The above description of the present disclosure is provided for the purpose of illustration, and it would be understood by a person with ordinary skill in the art that various changes and modifications may be made without changing technical conception and essential features of the present disclosure. Thus, it is clear that the above-described examples are illustrative in all aspects and do not limit the present disclosure. For example, each component described to be of a single type can be implemented in a distributed manner. Likewise, components described to be distributed can be implemented in a combined manner.

We claim:

1. A cosmetic composition for proliferating dermal papilla cells, comprising:
   heat-treated *Limosilactobacillus fermentum* LM1020 deposited under accession number KCCM12918P as an active ingredient.

2. The cosmetic composition for proliferating dermal papilla cells of claim 1, wherein the heat-treated *Limosilactobacillus fermentum* LM1020 is derived from fermented dough.

3. The cosmetic composition for proliferating dermal papilla cells of claim 1, wherein the heat-treated *Limosilactobacillus fermentum* LM1020 has a ratio of saturated fatty acids:unsaturated fatty acids:cyclic fatty acids of 0.1 to 2:0.25 to 5:0.03 to 0.6.

4. The cosmetic composition for proliferating dermal papilla cells of claim 1, wherein the heat-treated *Limosilac-*

*tobacillus fermentum* LM1020 increases the expression of CDK2, CDK4, cyclin B1, and cyclin D1.

5. The cosmetic composition for proliferating dermal papilla cells of claim 1, wherein the heat-treated *Limosilactobacillus fermentum* LM1020 reduces a gene expression level of 5α-reductase-1 and increases gene expression levels of FGF7, FGF10, and EGF.

6. The cosmetic composition for proliferating dermal papilla cells of claim 1, further comprising:

L-menthol, salicylic acid, and dexpanthenol.

7. The cosmetic composition for proliferating dermal papilla cells of claim 6, wherein the heat-treated *Limosilactobacillus fermentum* LM1020 has a concentration of $1 \times 10^6$ cells/mL or $1 \times 10^7$ cells/mL.

8. The cosmetic composition for proliferating dermal papilla cells of claim 6, further comprising:

purified water, ethanol, alanine/histidine/lysine polypeptide copper (HCl), polyacrylate crosspolymer-6, coconut acid, proline, tea tree oil, glycerin, peptide, butylene glycol, 1,2-hexanediol, green tea extracts, lavender flower extracts, quince extracts, and ethyl hexanediol.

9. The cosmetic composition for proliferating dermal papilla cells of claim 8, wherein the cosmetic composition for proliferating dermal papilla cells increases microbial diversity and lactic acid bacteria diversity of the scalp.

10. A food composition for proliferating dermal papilla cells, comprising:

heat-treated *Limosilactobacillus fermentum* LM1020 deposited under accession number KCCM12918P as an active ingredient.

11. The food composition for proliferating dermal papilla cells of claim 10, wherein the heat-treated *Limosilactobacillus fermentum* LM1020 is derived from fermented dough.

12. The food composition for proliferating dermal papilla cells of claim 10, wherein the heat-treated *Limosilactobacillus fermentum* LM1020 has a ratio of saturated fatty acids:unsaturated fatty acids:cyclic fatty acids of 0.1 to 2:0.25 to 5:0.03 to 0.6.

13. A pharmaceutical composition for treating hair loss, comprising:

heat-treated *Limosilactobacillus fermentum* LM1020 deposited under accession number KCCM12918P as an active ingredient.

14. The pharmaceutical composition for treating hair loss of claim 13, wherein the heat-treated *Limosilactobacillus fermentum* LM1020 is derived from fermented dough.

15. The pharmaceutical composition for treating hair loss of claim 13, wherein the heat-treated *Limosilactobacillus fermentum* LM1020 has a ratio of saturated fatty acids: unsaturated fatty acids:cyclic fatty acids of 0.1 to 2:0.25 to 5:0.03 to 0.6.

16. The pharmaceutical composition for treating hair loss of claim 13, wherein the heat-treated *Limosilactobacillus fermentum* LM1020 increases the expression of CDK2, CDK4, cyclin B1, and cyclin D1.

17. The pharmaceutical composition for treating hair loss of claim 13, wherein the heat-treated *Limosilactobacillus fermentum* LM1020 reduces a gene expression level of 5α-reductase-1 and increases gene expression levels of FGF7, FGF10, and EGF.

\* \* \* \* \*